US009028859B2

(12) United States Patent
Hossainy et al.

(10) Patent No.: US 9,028,859 B2
(45) Date of Patent: May 12, 2015

(54) PHASE-SEPARATED BLOCK COPOLYMER COATINGS FOR IMPLANTABLE MEDICAL DEVICES

(75) Inventors: Syed F. A. Hossainy, Fremont, CA (US); Thierry Glauser, Redwood City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1362 days.

(21) Appl. No.: 11/482,599

(22) Filed: Jul. 7, 2006

(65) Prior Publication Data

US 2008/0008739 A1    Jan. 10, 2008

(51) Int. Cl.
| | |
|---|---|
| *A61F 2/00* | (2006.01) |
| *A61L 31/16* | (2006.01) |
| *A61L 31/04* | (2006.01) |
| *A61L 31/10* | (2006.01) |

(52) U.S. Cl.
CPC ............... *A61L 31/16* (2013.01); *A61L 31/048* (2013.01); *A61L 31/10* (2013.01); *A61L 2300/606* (2013.01); *A61L 2420/08* (2013.01)

(58) Field of Classification Search
None
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 2,968,649 A | 1/1961 | Pailthorp et al. | |
| 3,051,677 A | 8/1962 | Rexford | |
| 3,178,399 A | 4/1965 | Lo | |
| 3,324,069 A | 6/1967 | Koblitz et al. | |
| 3,773,737 A | 11/1973 | Goodman et al. | |
| 3,779,805 A | 12/1973 | Alsberg | |
| 3,849,514 A | 11/1974 | Gray, Jr. et al. | |
| 3,856,827 A | 12/1974 | Cavitt | |
| 4,076,929 A | 2/1978 | Dohany | |
| 4,197,380 A | 4/1980 | Chao et al. | |
| 4,226,243 A | 10/1980 | Shalaby et al. | |
| 4,304,010 A | 12/1981 | Mano | |
| 4,304,767 A | 12/1981 | Heller et al. | |
| 4,329,383 A | 5/1982 | Joh | |
| 4,343,931 A | 8/1982 | Barrows | |
| 4,346,710 A | 8/1982 | Thanawalla et al. | |
| 4,353,960 A | 10/1982 | Endo et al. | |
| 4,399,264 A | 8/1983 | Squire | |
| 4,413,359 A | 11/1983 | Akiyama et al. | |
| 4,423,183 A | 12/1983 | Close | |
| 4,485,250 A | 11/1984 | Squire | |
| 4,529,792 A | 7/1985 | Barrows | |
| 4,530,569 A | 7/1985 | Squire | |
| 4,564,013 A | 1/1986 | Lilenfeld et al. | |
| 4,569,978 A | 2/1986 | Barber | |
| 4,611,051 A | 9/1986 | Hayes et al. | |
| 4,632,842 A | 12/1986 | Karwoski et al. | |
| 4,636,346 A | 1/1987 | Gold et al. | |
| 4,656,242 A | 4/1987 | Swan et al. | |
| 4,718,907 A | 1/1988 | Karwoski et al. | |
| 4,733,665 A | 3/1988 | Palmaz | |
| 4,749,585 A | 6/1988 | Greco et al. | |
| 4,754,009 A | 6/1988 | Squire | |
| 4,770,939 A | 9/1988 | Sietses et al. | |
| 4,800,882 A | 1/1989 | Gianturco | |
| 4,871,357 A | 10/1989 | Hsu et al. | |
| 4,876,109 A | 10/1989 | Mayer et al. | |
| 4,882,168 A | 11/1989 | Casey et al. | |
| 4,886,062 A | 12/1989 | Wiktor | |
| 4,897,457 A | 1/1990 | Nakamura et al. | |
| 4,908,404 A | 3/1990 | Benedict et al. | |
| 4,910,276 A | 3/1990 | Nakamura et al. | |
| 4,931,287 A | 6/1990 | Bae et al. | |
| 4,935,477 A | 6/1990 | Squire | |
| 4,941,870 A | 7/1990 | Okada et al. | |
| 4,948,851 A | 8/1990 | Squire | |
| 4,973,142 A | 11/1990 | Squire | |
| 4,975,505 A | 12/1990 | Squire | |
| 4,977,008 A | 12/1990 | Squire | |
| 4,977,025 A | 12/1990 | Squire | |
| 4,977,026 A | 12/1990 | Squire | |
| 4,977,297 A | 12/1990 | Squire | |
| 4,977,901 A | 12/1990 | Ofstead | |
| 4,982,056 A | 1/1991 | Squire | |
| 4,985,308 A | 1/1991 | Squire | |
| 4,999,248 A | 3/1991 | Squire | |
| 5,000,547 A | 3/1991 | Squire | |

(Continued)

FOREIGN PATENT DOCUMENTS

| | | |
|---|---|---|
| DE | 42 24 401 | 1/1994 |
| DE | 19723723 A1 | 12/1998 |

(Continued)

OTHER PUBLICATIONS

Iannelli et al. Selective Microwave-Accelerated Synthesis and Polymerization of Chiral Methacrylamide Directly From Methacrylic Acid and (R)-1-Phenyl-Ethylamine. 2004.*
International Search Report for PCT/US2007/015569 filed Jul. 5, 2007, mailed Nov. 30, 2007, 13 pgs.
U.S. Appl. No. 09/966,036, filed Sep. 28, 2001, Happ.
U.S. Appl. No. 10/176,504, filed Jun. 21, 2002, Roorda et al.
U.S. Appl. No. 10/176,510, filed Jun. 21, 2002, Hossainy et al.
U.S. Appl. No. 10/177,117, filed Jun. 21, 2002, Hossainy.
U.S. Appl. No. 10/177,154, filed Jun. 21, 2002, Hossainy et al.

(Continued)

*Primary Examiner* — Scott Long
*Assistant Examiner* — Sarah Alawadi
(74) *Attorney, Agent, or Firm* — Squire Patton Boggs (US) LLP

(57) ABSTRACT

Medical devices and coatings for medical devices are disclosed, including methods for forming the devices and coatings. The devices and coatings comprise a phase-separated block copolymer matrix and one or more active agents. The phase-separated block copolymer matrix can be used to modulate the release-rate of one or more active agents from the medical device.

21 Claims, No Drawings

(56) References Cited

U.S. PATENT DOCUMENTS

| | | |
|---|---|---|
| 5,006,382 A | 4/1991 | Squire |
| 5,019,096 A | 5/1991 | Fox, Jr. et al. |
| 5,030,394 A | 7/1991 | Sietses et al. |
| 5,047,020 A | 9/1991 | Hsu |
| 5,051,114 A | 9/1991 | Nemser et al. |
| 5,051,978 A | 9/1991 | Mayer et al. |
| 5,053,048 A | 10/1991 | Pinchuk |
| 5,076,659 A | 12/1991 | Bekiarian et al. |
| 5,093,427 A | 3/1992 | Barber |
| 5,100,992 A | 3/1992 | Cohn et al. |
| 5,107,852 A | 4/1992 | Davidson et al. |
| 5,110,645 A | 5/1992 | Matsumoto et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,176,972 A | 1/1993 | Bloom et al. |
| 5,185,408 A | 2/1993 | Tang et al. |
| 5,219,980 A | 6/1993 | Swidler |
| 5,246,451 A | 9/1993 | Trescony et al. |
| 5,258,020 A | 11/1993 | Froix |
| 5,272,012 A | 12/1993 | Opolski |
| 5,276,121 A | 1/1994 | Resnick |
| 5,292,516 A | 3/1994 | Viegas et al. |
| 5,296,283 A | 3/1994 | Froggatt |
| 5,298,260 A | 3/1994 | Viegas et al. |
| 5,300,295 A | 4/1994 | Viegas et al. |
| 5,302,385 A | 4/1994 | Khan et al. |
| 5,306,501 A | 4/1994 | Viegas et al. |
| 5,306,786 A | 4/1994 | Moens et al. |
| 5,308,685 A | 5/1994 | Froggatt |
| 5,310,838 A | 5/1994 | Hung et al. |
| 5,324,889 A | 6/1994 | Resnick |
| 5,326,839 A | 7/1994 | Resnick |
| 5,328,471 A | 7/1994 | Slepian |
| 5,330,768 A | 7/1994 | Park et al. |
| 5,336,518 A | 8/1994 | Narayanan et al. |
| 5,338,608 A | 8/1994 | Resnick |
| 5,342,348 A | 8/1994 | Kaplan |
| 5,353,368 A | 10/1994 | Resnick |
| 5,354,910 A | 10/1994 | Hung et al. |
| 5,368,566 A | 11/1994 | Crocker |
| 5,380,299 A | 1/1995 | Fearnot et al. |
| 5,383,853 A | 1/1995 | Jung et al. |
| 5,383,928 A | 1/1995 | Scott et al. |
| 5,395,311 A | 3/1995 | Andrews |
| 5,403,341 A | 4/1995 | Solar |
| 5,408,020 A | 4/1995 | Hung et al. |
| 5,417,969 A | 5/1995 | Hsu et al. |
| 5,417,981 A | 5/1995 | Endo et al. |
| 5,443,458 A | 8/1995 | Eury |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,545,208 A | 8/1996 | Wolff et al. |
| 5,560,463 A | 10/1996 | Link et al. |
| 5,562,734 A | 10/1996 | King |
| 5,569,463 A | 10/1996 | Helmus et al. |
| 5,575,818 A | 11/1996 | Pinchuk |
| 5,578,073 A | 11/1996 | Haimovich et al. |
| 5,581,387 A | 12/1996 | Cahill |
| 5,584,877 A | 12/1996 | Miyake et al. |
| 5,591,224 A | 1/1997 | Schwartz et al. |
| 5,604,283 A | 2/1997 | Wada et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,616,608 A | 4/1997 | Kinsella et al. |
| 5,624,411 A | 4/1997 | Tuch |
| 5,628,728 A | 5/1997 | Tachibana et al. |
| 5,628,730 A | 5/1997 | Shapland et al. |
| 5,632,771 A | 5/1997 | Boatman et al. |
| 5,632,776 A | 5/1997 | Kurumatani et al. |
| 5,632,840 A | 5/1997 | Campbell |
| 5,635,201 A | 6/1997 | Fabo |
| 5,644,020 A | 7/1997 | Timmermann et al. |
| 5,649,977 A | 7/1997 | Campbell |
| 5,658,995 A | 8/1997 | Kohn et al. |
| 5,665,428 A * | 9/1997 | Cha et al. .................... 427/213.3 |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,684,061 A | 11/1997 | Ohnishi et al. |
| 5,691,311 A | 11/1997 | Maraganore et al. |
| 5,697,967 A | 12/1997 | Dinh et al. |
| 5,700,286 A | 12/1997 | Tartaglia et al. |
| 5,702,754 A | 12/1997 | Zhong |
| 5,711,958 A | 1/1998 | Cohn et al. |
| 5,713,949 A | 2/1998 | Jayaraman |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,750,234 A | 5/1998 | Johnson et al. |
| 5,758,205 A | 5/1998 | Hara et al. |
| 5,759,205 A | 6/1998 | Valentini |
| 5,760,118 A | 6/1998 | Sinclair et al. |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,804,318 A | 9/1998 | Pinchuk et al. |
| 5,820,917 A | 10/1998 | Tuch |
| 5,824,048 A | 10/1998 | Tuch |
| 5,824,049 A | 10/1998 | Ragheb et al. |
| 5,827,587 A | 10/1998 | Fukushi |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,857,998 A | 1/1999 | Barry |
| 5,858,746 A | 1/1999 | Hubbell et al. |
| 5,858,990 A | 1/1999 | Walsh |
| 5,860,963 A | 1/1999 | Azam et al. |
| 5,861,168 A | 1/1999 | Cooke et al. |
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,874,165 A | 2/1999 | Drumheller |
| 5,876,433 A | 3/1999 | Lunn |
| 5,877,224 A | 3/1999 | Brocchini et al. |
| 5,879,697 A | 3/1999 | Ding et al. |
| 5,879,713 A | 3/1999 | Roth et al. |
| 5,897,911 A | 4/1999 | Loeffler |
| 5,900,425 A | 5/1999 | Kanikanti et al. |
| 5,902,875 A | 5/1999 | Roby et al. |
| 5,905,168 A | 5/1999 | Dos Santos et al. |
| 5,910,564 A | 6/1999 | Gruning et al. |
| 5,911,704 A | 6/1999 | Humes |
| 5,914,387 A | 6/1999 | Roby et al. |
| 5,919,893 A | 7/1999 | Roby et al. |
| 5,921,933 A | 7/1999 | Sarkis et al. |
| 5,922,393 A | 7/1999 | Jayaraman |
| 5,925,720 A | 7/1999 | Kataoka et al. |
| 5,928,279 A | 7/1999 | Shannon et al. |
| 5,932,299 A | 8/1999 | Katoot |
| 5,945,115 A | 8/1999 | Dunn et al. |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |

(56) References Cited

U.S. PATENT DOCUMENTS

| | | |
|---|---|---|
| 6,001,382 A | 12/1999 | Levy |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,033,724 A | 3/2000 | Molitor |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,060,534 A | 5/2000 | Ronan et al. |
| 6,080,488 A | 6/2000 | Hostettler et al. |
| 6,090,134 A | 7/2000 | Tu et al. |
| 6,096,070 A | 8/2000 | Ragheb et al. |
| 6,096,396 A | 8/2000 | Patton et al. |
| 6,096,798 A | 8/2000 | Luthra et al. |
| 6,096,809 A | 8/2000 | Lorcks et al. |
| 6,099,562 A | 8/2000 | Ding et al. |
| 6,099,563 A | 8/2000 | Zhong |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,124,045 A | 9/2000 | Soda et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,179,817 B1 | 1/2001 | Zhong |
| 6,180,632 B1 | 1/2001 | Myers et al. |
| 6,197,051 B1 | 3/2001 | Zhong |
| 6,203,551 B1 | 3/2001 | Wu |
| 6,211,249 B1 | 4/2001 | Cohn et al. |
| 6,214,901 B1 | 4/2001 | Chudzik et al. |
| 6,224,894 B1 | 5/2001 | Jamiolkowski et al. |
| 6,231,590 B1 | 5/2001 | Slaikeu et al. |
| 6,231,600 B1 | 5/2001 | Zhong |
| 6,240,616 B1 | 6/2001 | Yan |
| 6,242,041 B1 | 6/2001 | Katoot et al. |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,273,913 B1 | 8/2001 | Wright et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,362,271 B1 | 3/2002 | Lin et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,408,878 B2 | 6/2002 | Unger et al. |
| 6,410,612 B1 | 6/2002 | Hatanaka |
| 6,419,692 B1 | 7/2002 | Yang et al. |
| 6,451,373 B1 | 9/2002 | Hossainy et al. |
| 6,464,683 B1 | 10/2002 | Samuelson et al. |
| 6,475,779 B2 | 11/2002 | Mathiowitz et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,545,097 B2 | 4/2003 | Pinchuk et al. |
| 6,551,708 B2 | 4/2003 | Tsuda et al. |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,613,432 B2 | 9/2003 | Zamora et al. |
| 6,616,765 B1 | 9/2003 | Hossainy et al. |
| 6,620,617 B2 | 9/2003 | Mathiowitz et al. |
| 6,623,448 B2 | 9/2003 | Slater |
| 6,625,486 B2 | 9/2003 | Lundkvist et al. |
| 6,641,611 B2 | 11/2003 | Jayaraman |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,689,350 B2 | 2/2004 | Uhrich |
| 6,695,920 B1 | 2/2004 | Pacetti et al. |
| 6,703,040 B2 | 3/2004 | Katsarava et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,730,064 B2 | 5/2004 | Ragheb et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,776,796 B2 | 8/2004 | Llanos et al. |
| 6,780,424 B2 | 8/2004 | Claude |
| 6,790,228 B2 | 9/2004 | Hossainy et al. |
| 6,824,559 B2 | 11/2004 | Michal |
| 6,861,088 B2 | 3/2005 | Weber et al. |
| 6,865,810 B2 | 3/2005 | Stinson |
| 6,869,443 B2 | 3/2005 | Buscemi et al. |
| 6,872,225 B1 | 3/2005 | Rowan et al. |
| 6,878,160 B2 | 4/2005 | Gilligan et al. |
| 6,887,270 B2 | 5/2005 | Miller et al. |

(56) References Cited

U.S. PATENT DOCUMENTS

| | | | |
|---|---|---|---|
| 6,887,485 B2 | 5/2005 | Fitzhugh et al. |
| 6,890,546 B2 | 5/2005 | Mollison et al. |
| 6,890,583 B2 | 5/2005 | Chudzik et al. |
| 6,899,731 B2 | 5/2005 | Li et al. |
| 6,908,624 B2 | 6/2005 | Hossainy et al. |
| 7,008,667 B2 | 3/2006 | Chudzik et al. |
| 7,364,748 B2 | 4/2008 | Claude |
| 7,776,926 B1 | 8/2010 | Hossainy et al. |
| 8,309,112 B2 | 11/2012 | Glauser et al. |
| 8,323,676 B2 | 12/2012 | Lim et al. |
| 2001/0007083 A1 | 7/2001 | Roorda |
| 2001/0014717 A1 | 8/2001 | Hossainy et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0090389 A1 | 7/2002 | Humes et al. |
| 2002/0091433 A1 | 7/2002 | Ding et al. |
| 2002/0094440 A1 | 7/2002 | Llanos et al. |
| 2002/0099438 A1 | 7/2002 | Furst |
| 2002/0111590 A1 | 8/2002 | Davila et al. |
| 2002/0122877 A1 | 9/2002 | Harish et al. |
| 2002/0123801 A1 | 9/2002 | Pacetti et al. |
| 2002/0133183 A1 | 9/2002 | Lentz et al. |
| 2002/0143386 A1 | 10/2002 | Davila et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0004563 A1 | 1/2003 | Jackson et al. |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065346 A1 | 4/2003 | Evens et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0077312 A1 | 4/2003 | Schmulewicz et al. |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2003/0216307 A1* | 11/2003 | Kohn et al. ............ 514/12 |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0102758 A1 | 5/2004 | Davila et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0100609 A1 | 5/2005 | Claude |
| 2005/0106210 A1 | 5/2005 | Ding et al. |
| 2005/0112170 A1 | 5/2005 | Hossainy et al. |
| 2005/0113903 A1 | 5/2005 | Rosenthal et al. |
| 2005/0277577 A1* | 12/2005 | Hunter et al. ............ 514/2 |
| 2006/0034888 A1 | 2/2006 | Pacetti et al. |
| 2006/0047095 A1 | 3/2006 | Pacetti |
| 2006/0088571 A1 | 4/2006 | Chen et al. |
| 2006/0171985 A1* | 8/2006 | Richard et al. ............ 424/423 |
| 2007/0178136 A1* | 8/2007 | Arney et al. ............ 424/426 |

FOREIGN PATENT DOCUMENTS

| | | | |
|---|---|---|---|
| EP | 0 301 856 | 2/1989 |
| EP | 0 396 429 | 11/1990 |
| EP | 0 514 406 | 11/1992 |
| EP | 0 568 310 | 11/1993 |
| EP | 0 604 022 | 6/1994 |
| EP | 0 623 354 | 11/1994 |
| EP | 0 633 032 | 1/1995 |
| EP | 0 665 023 | 8/1995 |
| EP | 0 701 802 | 3/1996 |
| EP | 0 716 836 | 6/1996 |
| EP | 0 747 069 | 12/1996 |
| EP | 0 809 999 | 12/1997 |
| EP | 0 815 803 | 1/1998 |
| EP | 0 832 655 | 4/1998 |
| EP | 0 850 651 | 7/1998 |
| EP | 0 879 595 | 11/1998 |
| EP | 0 893 108 | 1/1999 |
| EP | 0 910 584 | 4/1999 |
| EP | 0 923 953 | 6/1999 |
| EP | 0 947 205 | 10/1999 |
| EP | 0 950 385 | 10/1999 |
| EP | 0 950 386 | 10/1999 |
| EP | 0 953 320 | 11/1999 |
| EP | 0 970 711 | 1/2000 |
| EP | 0 968 688 | 1/2000 |
| EP | 0 970 711 | 1/2000 |
| EP | 0 982 041 | 3/2000 |
| EP | 0 997 115 | 5/2000 |
| EP | 1 023 879 | 8/2000 |
| EP | 1 023 879 | 8/2000 |
| EP | 1 192 957 | 4/2002 |
| EP | 1 273 314 | 1/2003 |
| EP | 1 440 698 | * 1/2004 | ............ A61L 31/10 |

(56) References Cited

FOREIGN PATENT DOCUMENTS

| | | |
|---|---|---|
| EP | 1 440 698 | 7/2004 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 92/05695 | 4/1992 |
| WO | WO 92/18320 | 10/1992 |
| WO | WO 94/02185 | 2/1994 |
| WO | WO 94/09760 | 5/1994 |
| WO | WO 95/10989 | 4/1995 |
| WO | WO 95/24929 | 9/1995 |
| WO | WO 96/21404 | 7/1996 |
| WO | WO 96/40174 | 12/1996 |
| WO | WO 97/10011 | 3/1997 |
| WO | WO 97/41164 | 11/1997 |
| WO | WO 97/45105 | 12/1997 |
| WO | WO 97/46590 | 12/1997 |
| WO | WO 98/08463 | 3/1998 |
| WO | WO 98/13405 | 4/1998 |
| WO | WO 98/17331 | 4/1998 |
| WO | WO 98/32398 | 7/1998 |
| WO | WO 98/36784 | 8/1998 |
| WO | WO 98/58680 | 12/1998 |
| WO | WO 99/01118 | 1/1999 |
| WO | WO 99/32051 | 7/1999 |
| WO | WO 99/38546 | 8/1999 |
| WO | WO 99/55396 | 11/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/27455 | 5/2000 |
| WO | WO 00/29043 | 5/2000 |
| WO | WO 00/32255 | 6/2000 |
| WO | WO 00/38754 | 7/2000 |
| WO | WO 00/41738 | 7/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/30403 | 5/2001 |
| WO | WO 01/45763 | 6/2001 |
| WO | WO 01/49338 | 7/2001 |
| WO | WO 01/49340 | 7/2001 |
| WO | WO 01/51027 | 7/2001 |
| WO | WO 01/74414 | 10/2001 |
| WO | WO 01/87342 | 11/2001 |
| WO | WO 01/87368 | 11/2001 |
| WO | WO 01/87372 | 11/2001 |
| WO | WO 01/87376 | 11/2001 |
| WO | WO 02/03890 | 1/2002 |
| WO | WO 02/24249 | 3/2002 |
| WO | WO 02/26139 | 4/2002 |
| WO | WO 02/26162 | 4/2002 |
| WO | WO 02/26271 | 4/2002 |
| WO | WO 02/26281 | 4/2002 |
| WO | WO 02/34311 | 5/2002 |
| WO | WO 02/47731 | 6/2002 |
| WO | WO 02/47732 | 6/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/022324 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2005/011770 | 2/2005 |
| WO | WO 2006/047378 | 5/2006 |
| WO | WO 2006/071860 | 7/2006 |
| WO | WO 2006/083904 | 8/2006 |

OTHER PUBLICATIONS

U.S. Appl. No. 10/198,912, filed Jul. 19, 2002, Ding et al.
U.S. Appl. No. 10/630,250, filed Jul. 30, 2002, Pacetti et al.
U.S. Appl. No. 10/251,111, filed Sep. 19, 2002, Hossainy et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/428,691 filed May 1, 2003, Pacetti.
U.S. Appl. No. 10/718,278, filed Nov. 19, 2003, Hossainy et al.
U.S. Appl. No. 10/719,516, filed Nov. 21, 2002, Tang et al.
U.S. Appl. No. 10/738,704, filed Dec. 16, 2003, Pacetti et al.
U.S. Appl. No. 10/741,214, filed Dec. 19, 2003, Pacetti et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/835,656, filed Apr. 30, 2004, Tang et al.
U.S. Appl. No. 10/855,294, filed May 26, 2004, Pacetti et al.
U.S. Appl. No. 10/931,927, filed Aug. 31, 2004, Pacetti.
U.S. Appl. No. 10/960,381, filed Oct. 6, 2004, DesNoyer et al.
U.S. Appl. No. 10/975,247, filed Oct. 27, 2004, DesNoyer et al.
U.S. Appl. No. 10/976,551, filed Oct. 29, 2004, DesNoyer et al.
U.S. Appl. No. 10/999,391, filed Nov. 29, 2004, Hossainy.
U.S. Appl. No. 11/023,837, filed Dec. 27, 2004, Hossainy.
U.S. Appl. No. 11/027,955, filed Dec. 30, 2004, Hossainy et al.
U.S. Appl. No. 11/035,816, filed Jan. 14, 2005, Hossainy et al.
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).
Anonymous, *Rolling Therapeutic Agent Loading Device for Therapeutic Agent Delivery of Coated Stent*, Research Disclosure, Publ., Hampshire, GB, No. 434, p. 975 (2000).
Aoyagi et al., *Preparation of cross-linked aliphatic polyester and application to thermo-responsive material*, Journal of Controlled Release 32:87-96 (1994).
Arnold et al., *Effects of environment on the creep properties of a poly(ethylmethacrylate) based bone cement* J. Mater. Sci: Mater. In Med., vol. 12, pp. 707-717 (2001).
Bellex International, CYTOP®, *Amorphous Fluorocarbon Polymer*, 1 page (no date).
Bellex International, *Selected CYTOP Physical Data*, 1 page (no date).
Bellex International, CYTOP®, http://www.bellexinternational.com/cytop.htm, printed Mar. 30, 2001, 1 page.
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.
Chung et al., *Inner core segment design for drug delivery control of thermo-responsive polymeric micelles*, Journal of Controlled Release 65:93-103 (2000).

(56) References Cited

OTHER PUBLICATIONS

Cífková et al., *Irritation effects of residual products derived from p(HEMA) gels*, Biomaterials, vol. 9, (Jul. 1998), pp. 372-375.
Dalsin et al., *DOPA: A New Anchor for PEGylation of Biomaterial Surfaces*, Soc. For Biomaterials 28th Annual Meeting Transactions, pp. 40 (2002).
Deb et al., *Effect of crosslinking agents on poly(ethylmethacrylate) bone cements*, J. of Mater.Sci: Mater. In Med., vol. 8, pp. 829-833 (1997).
Del Guerra et al., *In vitro biocompatibility of fluorinated polyurethanes*, J. Mater. Sci. In Med., vol. 5, pp. 452-456 (1994).
De Lezo et al., *Intracoronary Ultrasound Assessment of Directional Coronary Atherectomy: Immediate and Follow-Up Findings*, JACC vol. 21, No. 2, (1993) pp. 298-307.
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5)1347-1353 (Nov. 1989).
DuPont, *Teflon AF 1601S amorphous fluoropolymer solutions*, product information, 2 pages (1998).
DuPont, *Processing of Teflon® AF*, Teflon Amorphous Fluoropolymer, http://www.dupont.com/teflon/af/processing.html, printed Mar. 30, 2001, 1 page.
DuPont, *High-Performance/Potential Applications*, Teflon Amorphous Fluoropolymer, http://www.dupont.com/teflon/af/potapps.html, printed Mar. 30, 2001, 3 pages.
DuPont, *Performance Comparison of Teflon AF*, Teflon Amorphous Fluoropolymer, http://www.dupont.com/teflon/af/performance.html, printed Mar. 30, 2001, 3 pages.
DuPont, *Unique Properties of Teflon® AF*, Teflon Amorphous Fluoropolymer, http://www.dupont.com/teflon/af/unique.html, printed Mar. 30, 2001, 3 pages.
DuPont, *Teflon® AF: A New Generation of High-Performance Fluoropolymer Resins*, http://www.dupont.com/teflon/af/index.html, printed Mar. 30, 2001, 1 page.
DuPont, *Teflon® Protects Superconductors Against Acid*, Teflon Amorphous Fluoropolymer, http://www.dupont.com/teflon/af/superconductor.html, printed Sep. 21, 2004, 2 pages.
DuPont, *Available Grades of DuPont Teflon® AF*, Teflon Amorphous Fluoropolymer, http://www.dupont.com/teflon/af/grades.html, printed Sep. 21, 2004, 2 pages.
DuPont, *Teflon® AF amorphous fluoropolymers*, Product Information, 6 pages (1998).
DuPont, Sales Notice, Teflon Amorphous Fluoropolymer, http://www.dupont.com/teflon/af/oatent.html, printed Sep. 21, 2004, 2 pages.
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Fine et al., *Improved nerve regeneration through piezoelectric vinylidenefluoride-trifluoroethylene copolymer guidance channels*, Biomaterials, vol. 12, October, pp. 775-780 (1991).
Fischell, *Polymer Coatings for Stents*, Circulation, 94:1494-95 (1996).
Gullickson, *Reference Data Sheet on Common Chlorinated Solvents*, http://www.mcs.net/~hutter/tee/chlorina.html, •rinted Mar. 30, 2001, 5 pages.
Gunn et al., *Stent coatings and local drug delivery*, Eur. Heart J., vol. 20, issue 23, pp. 1693-1700 (1999).
Harper et al., *Fatigue Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.
Harper et al., *Mechanical properties of hydroxyapatite reinforced poly (ethyl methacrylate) bone cement after immersion in a physiological solution: influence of a silane coupling agent*, J. Mater. Sci.: Mater. In Med., vol. 11, pp. 491-497 (2000).

Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et-al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Kruft et al., *Studies on radio-opaque polymeric biomaterials with potential applications to endovascular prostheses*, Biomaterials, vol. 17, No. 18, pp. 1803-1812 (1996).
Lambert et al., *Localized Arterial Wall Drug Delivery From a Polymer-Coated Removable Metallic Stent*, Circulation, vol. 90, No. 2, pp. 1003-1011 (1994).
Laroche et al., *Polyvinylidene fluoride (PVDF) as a biomaterial: From polymeric raw material to monofilament vascular suture*, J. of Biomedical Mat. Research, vol. 29, pp. 1525-1536 (1995).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Lin et al., *Fluropolymer Alloys Performance Optimization of PVDF Alloys*, Fluropolymers 2 Properties, edited by Hougham et al., Plenum Publishers N.Y. pp. 121-136 (1999).
Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).
Luthra, Biointeractions Ltd (BIL), http://www.biomateria.com/biointeractions.html, printed Sep. 21, 2004, 3 pages.
3M, *Specialty Fluids 3M™ Fluorinert™ Liquids, Typical Properties*, http://www.3m.com/market/industrial/fluids/fluoprop.html, printed Mar. 30, 2001, 3 pages.
Materials Engineering, *Applications in Design/Manufacturing/R&D*, Materials Selector 1993, Penton Publishing (1992) 6 pgs.
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Medtronic, Trillium Affinity NT, Oxygenator, Product Information, 6 pages (2000).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Moreno et al., *Macrophage Infiltration Predicts Restenosis After Coronary Intervention in Patients with Unstable Angina*, Circulation, vol. 94, No. 12, (1996) pp. 3098-3102.
NCMS SOLV-DB, *Query Results for: CFC*, http://solvdb.ncms.org/CAT01.idc?chemcat=CFC, printed Mar. 30, 2001, 2 pages.
NCMS SOLV-DB, *Query Results for: FC-75 Fluorinert*, http://solvdb.ncms.org/common01.idc, printed Mar. 30, 2001, 2 pages.
Novick et al., *Protein-containing hydrophobic coatings and films*, Biomaterials, vol. 23, No. 2 (2002) pp. 441-448.
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

(56) References Cited

OTHER PUBLICATIONS

Oikawa et al., Mechanisms of Acute Gain and Late Lumen Loss After Atherectomy in Different Preintervention Arterial Remodeling Patterns, The Am. J. of Cardilogy, vol. 89, (2002) pp. 505-510.
Ozaki et al., New Stent Technologies, Progress in Cardiovascular Diseases, vol. XXXIX(2):129-140 (Sep./Oct. 1996).
Parkell, Inc., SNAP Powder-Liquid Temporary Crown and Bridge Resin, http://www.parkell.com/snap.html, printed Oct. 21, 2004, 1 pg.
Parkell, Inc., Material Safety Data Sheets, http://www.parkell.com/msds.html, printed Oct. 21, 2004, 2 pgs.
Parkell, Inc., MSDS No: S426, VAR, Material Safety Data Sheet, 2 pgs (2002).
Parkell, Inc., MSDS No: S441, Material Safety Data Sheet, 2 pgs (2002).
Pechar et al., Poly(ethylene glycol) Multiblock Copolymer as a Carrier of Anti-Cancer Drug Doxorubicin, Bioconjucate Chemistry 11(2):131-139 (Mar./Apr. 2000).
Peng et al., Role of polymers in improving the results of stenting in coronary arteries, Biomaterials 17:685-694 (1996).
Porté-Durrieu et al., Surface Treatment of Biomaterials by Gamma and Swift Heavy Ions Grafting, Nuclear Instruments and Methods in Physics Research, vol. B 151, pp. 404-415 (1999).
Porté-Durrieu et al., Development of "Heparin-Like" Polymers Using Swift Heavy Ion and Gamma Radiation. I. Preparation and Characterization of the Materials, Surface Treatment of Biomaterials, pp. 119-127 (2000).
Revell et al., Experimental Studies of the Biological Response to a New Bone Cement: II Soft Tissue Reactions in the Rat, Clinical Materials, vol. 10, pp. 233-238 (1992).
Saotome, et al., Novel Enzymatically Degradable Polymers Comprising α-Amino Acid, 1,2-Ethanediol, and Adipic Acid, Chemistry Letters, pp. 21-24, (1991).
Scully et al., Effect of a heparan sulphate with high affinity for antithrombin III upon inactivation of thrombin and coagulaton Factor Xa, Biochem J. 262, (1989) pp. 651-658.
Shigeno, Prevention of Cerebrovascular Spasm by Bosentan, Novel Endothelin Receptor, Chemical Abstract 125:212307 (1996).
Techspray, Flux Remover AMS, Product Information, http://www.techspray.com/1665info.htm, printed Aug. 28, 2001, 2 pages.
Teomin et Perivascular delivery of heparin for the reduction of smooth muscle cell proliferation after endothelial injury, J. of Controlled Release, vol. 60, pp. 129-142 (1999).
Topol et al., Frontiers in Interventional Cardiology, Circulation, vol. 98, pp. 1802-1820 (1998).
Urban et al., Why Make Monofilament Sutures Out of Polyvinylidene Fluoride?, ASAIO J., vol. 40, No. 2, pp. 145-156 (1994).
Verweire et al., Evaluation of fluorinated polymers as coronary stent coating, J. Mater.Sci: Mater. In Med., vol. 11, No. 4, pp. 207-212 (2000).

Virmani et al., Lessons From Sudden Coronary Death a Comprehensive Morphological Classification Scheme for Atherosclerotic Lesions, Arterioscler Thromb Vasc Biol. (2000) pp. 1262-1275.
va Beusekom et al., Coronary stent coatings, Coronary Artery Disease 5(7):590-596 (Jul. 1994).
Weightman et al., The Mechanical Properties of Cement and Loosening of the Femoral Component of Hip Replacements, J. Bone and Joint Surg., vol. 69-B, No. 4, pp. 558-564 (Aug. 1987).
Wholey et al., Global Experience in Cervical Carotid Artery Stent Placement, Catherization and Cardiovascular Inteventions, vol. 50, No. 2, pp. 160-167 (2000).
Wilensky et al., Methods and Devices for Local Drug Delivery in Coronary and Peripheral Arteries, Trends Cardiovasc. Med. 3(5):163-170 (1993).
Woo et al., Phase Behavior of Polycarbonate Blends with Selected Halogenated Polymers, J. Appl. Polym. Sci., vol. 30, pp. 4243-4249 (1985).
Yokoyama et al., Characterization of physical entrapment and chemical conjugation of adriamycin in polymeric micelles and their design for in vivo delivery to a solid tumor, Journal of Controlled Release 50:79-92 (1998).
International Search Report for PCT appl. PCT/US03/15347, filed May 14, 2003, date of mailing Sep. 4, 2003, 6 pgs.
International Search Report for PCT appl. PCT/US03/15544, filed May 14, 2003, date of mailing Jan. 23, 2004, 9 pgs.
International Search Report for PCT appl. PCT/US03/28643, filed Sep. 10, 2003, date of mailing Mar. 12, 2003, 10 pgs.
International Search Report for PCT appl. PCT/US03/21170, filed Jul. 2, 2003, date of mailing Oct. 31, 2003, 8 pgs.
Translation of the Notice of Reasons for Rejection from JPO dispatched Oct. 30, 2012, 5 pgs.
Hanefeld et al., "Coating of Poly(p-xylylene) by PLA-PEO-PLA Triblock Copolymers with Excellent Polymer-Polymer Adhesion for Stent Applications", Biomacromolecules 7, pp. 2086-2090, (2006).
Richard et al., "Evaluation of Acrylate-Based Block Copolymers Prepared by Atom Transfer Radical Polymerization as Matrices for Paclitaxel Delivery from Coronary Stents", Biomacromolecules 6, pp. 3410-3418 (2005).
Sipos et al., "Controlled Delivery of Paclitaxel from Stent Coatings Using Poly(hydroxystyrene-b-isobutylene-b-hydroxystyrene) and Its Acetylated Derivative", Biomacromolecules 6, (5), pp. 2570-2582 (2005).
Zentner et al., "Bodegradable block copolymers for delivery of proteins and water-insoluble drugs", J. of Controlled Release 72, pp. 203-215 (2001).
Zhou et al., "Syntheses and Characterization of Poly(cyclohexyl vinyl ether-stat-vinyl alcohol)-b-polyisobutelene-b-poly(cyclohexyl vinyl ether-stat-vinyl alcohol) Tiblock Copolymers and Their Application as Coatings to Deliver Paclitaxel from Coronary Stents", Macromolecules 38, pp. 8183-8191 (2005).

* cited by examiner

PHASE-SEPARATED BLOCK COPOLYMER COATINGS FOR IMPLANTABLE MEDICAL DEVICES

TECHNICAL FIELD

The present invention relates generally to the field of medical devices, particularly implantable medical devices, comprising a phase-separated block copolymer and one or more active agents. More particularly, this invention pertains to methods for modulating the release-rate of active agents from a block copolymer by tailoring the phase-separation of the block copolymer and the phase into which the active agent is incorporated. This invention further pertains to methods for making medical devices and coatings for medical devices comprising a phase-separated block copolymer and one or more active agents.

BACKGROUND OF THE INVENTION

In the field of medical devices, particularly medical devices that are implantable within a subject, predictable and controllable performance is essential to the successful treatment of a patient. An example of an implantable medical device is a stent. Stents can act as a mechanical means to physically hold open and, if desired, expand a passageway within a subject. Typically, a stent is compressed, inserted into a small vessel through a catheter, and then expanded to a larger diameter once placed in a proper location. Stents play an important role in a variety of medical procedures such as, for example, percutaneous transluminal coronary angioplasty (PTCA), a procedure used to treat heart disease by opening a coronary artery blocked by an occlusion. Stents are generally implanted in such procedures to reduce occlusion formation, inhibit thrombosis and restenosis, and maintain patency within vascular lumens. Examples of patents disclosing stents include U.S. Pat. No. 4,733,665 to Palmaz, U.S. Pat. No. 4,800,882 to Gianturco, and U.S. Pat. No. 4,886,062 to Wiktor.

Stents and other medical devices are also being developed to locally deliver active agents, e.g. drugs or other medically beneficial materials. Local delivery is often preferred over systemic delivery, particularly where high systemic doses are necessary to affect a particular site. For example, agent-coated stents have demonstrated dramatic reductions in stent restenosis rates by inhibiting tissue growth associated with restenosis.

Proposed local delivery methods from medical devices include coating the device surface with a layer comprising a polymeric matrix and attaching an active agent to the polymer backbone or incorporating the active agent by dispersing, impregnating or trapping it in the polymeric matrix. For example, one method of applying an active agent to a stent involves blending the agent with a polymer dissolved in a solvent, applying the composition to the surface of the stent, and removing the solvent to leave a polymer matrix in which an active agent is impregnated, dispersed or trapped. Once the medical device, for example a stent, has been implanted at the treatment site, the active agent has a release-rate profile from the polymer matrix that is dependent upon a variety of factors including, for example, the composition of the polymer matrix and the active agent.

It is highly desirable to be able to modulate active-agent release-rates from a polymer matrix to provide the most medically efficacious treatment. For example, in a polymer coating for a stent comprising more than one active agent it may be desirable that one of the active agents have a slower or faster release-rate from the polymer matrix, or to maintain a concentration of one or more of the active agents at a therapeutically effective level for a prolonged period of time. Those skilled in the art will therefore appreciate that local delivery of active agents would benefit not only from improved release-rate profiles that are controllable and predictable, but also from release-rate profiles that can be tailored to the particular medical treatment.

The embodiments of the present invention address such needs, as well as others, by providing methods for modulating and/or controlling the release-rates of active agents from medical devices and coatings for medical devices.

SUMMARY OF THE INVENTION

According to one aspect of the invention, a medical device comprising a phase-separated block copolymer and one or more active agents is provided. Also provided are coatings for medical devices comprising a phase-separated block copolymer and one or more active agents. Phase-separation of the block copolymer is used to modulate the release-rates of active agents from medical devices and coating layers for medical devices. In one embodiment, the release-rates of active agents from the coating layers can be modulated by controlling the phase domain into which the active agent dissolves or is otherwise incorporated.

The phase-separated block copolymers of the invention comprise two or more blocks phase separated into two or more phase domains. Active agents can be incorporated into one of the phase domains. In one embodiment, the phase-separated block copolymer comprises one or more phase domains selected from the group consisting of hard phase domains, soft phase domains, crystalline phase domains, hydrogen bonded phase domains, Π-Π stacked phase domains, hydrophilic phase domains, hydrophobic phase domains, and non-crystalline phase domains. In some embodiments, the phase-separated block copolymer comprises a hydrophilic block. In some embodiments, the phase-separated block copolymer comprises a hydrophilic block and a hydrophobic block. In other embodiments, the phase-separated block copolymer comprises two or more hydrophobic blocks. In one embodiment, the phase-separated block copolymer comprises a hydrogen bonded phase domain, wherein the hydrogen bonded phase domain preferentially incorporates active agents that can form hydrogen bonds.

Methods for fabricating a coating for a medical device comprising a phase-separated block copolymer and one or more active agents is also provided. In one embodiment, the method comprises depositing a coating composition on at least a portion of the device, the coating composition comprising a block copolymer including at least two blocks and one or more active agents, wherein the block copolymer phase-separates into two or more phase domains.

DETAILED DESCRIPTION

The present invention generally pertains to methods for modulating the release-rate of active agents from medical devices comprising a phase-separated block copolymer and one or more active agents. The present invention also pertains to medical devices with enhanced bio-beneficial properties and mechanical properties. In one embodiment, a phase-separated block copolymer and one or more active agents are used in the fabrication of a medical device, such as a fully absorbable stent. In other embodiments, the medical device includes a substrate (made from, for example, metal and/or polymer) and a coating comprising the phase-separated block copolymer and one or more active agents disposed on at least a portion of the substrate. In preferred embodiments, the medical device is a stent.

The medical devices and coatings for medical devices of the present invention comprise a phase-separated block copolymer and one or more active agents. The phase-separated block copolymers comprise two or more polymer blocks, which phase-separate into two or more phase domains. The phase-separation that occurs between the blocks of the copolymer can be tailored to provide an inhomogeneous material with unique physical and mechanical properties. In particular, the release-rates of active agents from the medical devices can be modulated by tailoring the phase-separation and the physical, chemical and mechanical properties of the copolymer blocks. The phase-separation of the block copolymer and the preferential incorporation of an active agent in one of the phase domains formed can be used, in some embodiments, to modulate the release-rates of the active agent. Invention embodiments can be used to either increase or decrease the release-rate of an active agent from a medical device, or to provide medical devices comprising two or more active agents where one active agent has a fast release rate and another active agent has a slow release rate. For example, in a phase-separated block copolymer comprising hydrophobic and hydrophilic phase domains an active agent that is hydrophobic, such as everolimus, will dissolve in the hydrophobic phase while a hydrophilic active agent, such as a peptide, will preferentially be incorporated into the hydrophilic phase. The hydrophobic phase domains will slowly release everolimus, while the hydrophilic peptide will be released more quickly from the hydrophilic phase domains, providing a coating layer with a release-rate profile that has two different release-rates. Further, the phase-separated block copolymer of the present invention can be used to incorporate otherwise incompatible active agents in the coating layers of the present invention. For example, an organic solvent based coating composition can be designed to accommodate a hydrophilic active agent by using a block copolymer comprising a hydrophilic block that forms micelles which allows the hydrophilic active agent to stay in solution. The polymer coating composition can be spray coated, for example, onto a medical device substrate where the block copolymer will phase-separate into hydrophilic phase domains containing the hydrophilic active agent.

While embodiments of the present invention are described below in conjunction with a coating for a medical device, such as a stent, the embodiments are equally applicable to the fabrication of medical devices, such as a fully absorbable stent, from the phase-separated block copolymer compositions and methods described herein.

Release-Rates

"Fast release' is defined as in vivo release (such as, for example, in a blood vessel of a living mammal) of all or substantially the entire amount of an active from the medical device or coating in less than 15 days, for example, within 7 to 14 days. "Slow release" is defined as in vivo release (such as, for example, in a blood vessel of a living mammal) all or substantially the entire amount of an active agent from the medical device or coating in 15 days or longer, for example, within 15 to 56 days. If the fast release is within 24 hours, such as less than 12 hours, 6 hours, 3 hours, or 1 hour the fast release can be defined as a "burst release." Coatings of the present invention can be modified to have any one or a combination of such release profiles for a single drug or different drugs. For example, a single drug can have a burst release and a slow release profile. As another example, drug A can have a burst release profile while drug B has a slow release profile.

By using phase-separation of the block copolymer matrix the release-rates of active agents can be more effectively engineered to provide greater medical benefits in the treatment of a patient. For example, fast release may be recommended for antimigratory active agents that often need to be released within 1 to 2 weeks. In contrast, antiproliferative active agents may need slow release, for example up to 30 days release time.

Block Copolymers

The term "block-copolymer" as used herein is defined in accordance with the terminology used by the International Union for Pure and Applied Chemistry (IUPAC). "Block-copolymer" refers to a copolymer containing a linear arrangement of blocks. The block is defined as a portion of a polymer molecule in which the monomeric units have at least one constitutional or configurational feature absent from the adjacent portions.

The term "block copolymer" is intended to broadly include polymers with two or more types of blocks such as di-block, tri-blocks, tetra-blocks, and so on. For example, a block copolymer of moiety A and moiety B may be written as -A-A-A-B-B-B-B-. Such a block copolymer is often referred to as an "AB block copolymer" or "di-block copolymer." The blocks need not be linked on the ends, since the individual blocks are usually long enough to be considered polymers in their own right. In addition to AB block copolymers, variations of other block copolymers include ABA block copolymers (-A-A-A-B-B-B-A-A-A-), ABCBA block copolymers (-A-A-A-B-B-B-C-C-C-B-B-B-A-A-A-), ABC block copolymers (-A-A-A-B-B-B-C-C-C-), etc. In preferred embodiments, the block copolymers are di-block (AB) or tri-block (ABA or ABC) copolymers.

The term "AB block-copolymer" is defined as a block-copolymer having moieties A and B arranged according to the general formula $-\{[A-]_m-[B]_n\}-_x$, where each of "m," "n," and "x" is a positive integer, and m≥2, and n≥2.

The term "ABA block-copolymer" is defined as a block-copolymer having moieties A and B arranged according to the general formula $-\{[A-]_m-[B-]_n-[A]_p\}-_x$, where each of "m," "n," "p," and "x" is a positive integer, and m≥2, and n≥2, and p≥2.

The term "ABC block-copolymer" is defined as a block-copolymer having moieties A, B, and C arranged according to the general formula $-\{[A-]_m-[B-]_n-[C]_p\}_x-$ where each of "m," "n," "p," and "x" is a positive integer, and m≥2, and n≥2, and p≥2.

The term "moiety" is defined as a portion of a complete structure of a copolymer, the portion to include at least 2 atoms joined together in a particular way. The term "moiety" includes functional groups and/or discreet bonded residues that are present in the macromolecule of a copolymer. The term "moiety" as used herein is inclusive of entire polymeric blocks in the block-copolymers. The term "moiety" can also be used to refer to individual units, for example monomer units, of a copolymer block.

The blocks of the block-copolymers need not be linked on the ends, since the values of the integers, determining the number of blocks, are such as to ensure that the individual blocks are usually long enough to be considered polymers in their own right. Accordingly, an ABA block copolymer can be named poly A-block-poly B-block-poly A-block-copolymer, an ABC block copolymer can be named poly A-block-poly B-block-poly C copolymer and an AB block copolymer can be named poly A-block-poly B-copolymer. Blocks "A," "B," and "C," typically larger than three-block size, can be alternating or random.

The term "random copolymer" is defined in accordance with terminology used by the IUPAC. "Random copolymer" refers to a copolymer consisting of macromolecules in which the probability of finding a given monomeric unit at any given site in the chain is independent of the nature of the adjacent units. In a random copolymer, the sequence distribution of monomeric units follows Bernoullian statistics.

Synthesize of Block Copolymers

Block copolymers useful in the present invention can be synthesized by common methods known to those having ordinary skill in the art. For example, block copolymers can be synthesized by radical copolymerization of monomers forming A-, B- and/or C-units in bulk, solution, suspension, or emulsion, in the presence of suitable initiators. One synthetic method that can be used is the method of living free radical copolymerization of a plurality of monomers with initiating-transfer agent termination of the living macro-chains (the inferter process) as described in U.S. patent application Ser. No. 10/746,483 (U.S. Pat. Publication No. 2005/1047647) to Glauser et al. and U.S. patent application Ser. No. 10/317,435 (U.S. Pat. No. 7,776,926) to Hossainy et al., the disclosures of which are incorporated herein by reference in their entirety. The inferter process utilizes an initiator capable of undergoing thermal and/or photolytic free radical decomposition. Examples of suitable initiators include benzyl-N,N-diethyldithiocarbamate (BDC) or p-xylylene-N,N-diethyldithiocarbamate (XDC). BDC is a derivative of toluene and has the formula $C_6H_5-CH_2-S-C(S)-N-(C_2H_5)_2$ and XDC is a derivative of p-xylene and has the formula $(C_2H_5)_2-N-C(S)-S-CH_2-C_6H_4-CH_2-S-C(S)-N-(C_2H_5)_2$. BCD and XCD can be prepared synthetically, as described for example in U.S. patent application Ser. No. 10/317,435 and U.S. Application Publication No. 2005/0147647, the disclosures of which are incorporated herein by reference. Other methods of synthesis of block copolymers include, but are not limited to, copolycondensation reactions catalyzed if necessary by an acid or base as known to one skilled in the art.

A wide variety starting moieties or monomers can be used to synthesize block copolymers of the present invention. Useful starting monomers from which the blocks of the block copolymers can be derived include, but are not limited to, unsaturated monomers, for example unsubstituted or substituted acrylates or vinyl monomers having a general formula $CH_2=CX-M$, where X is hydrogen or methyl and M is a substituted or unsubstituted aromatic group, aryl group or an ester group $O=C(OR)-$, where R is alkyl, aryl, hydrogen, or hydroxyalkyl group. Examples of unsubstituted or substituted acrylates or vinyl monomers, include, but are not limited to methyl methacrylate (MMA), ethyl methacrylate (EMA), n-butyl methacrylate (BMA), lauryl methacrylate (LMA), styrene (vinyl benzene) (ST), 2-hydroxyethyl methacrylate (HEMA), acrylic acid, methacrylic acid, N-vinyl pyrrolidone (VP), poly(ethylene glycol)-acrylate (PEGA), polyethylene glycol (PEG), 2-methacryloylethyl phosphoryl choline, phosphoryl choline methacrylate, 2-acrylamido-2-methyl-1-propanesulfonic acid, 3-sulfopropyl acrylate, 3-sulfopropyl methacrylate (SPMA), vinylsulfonic acid, 4-styrenesulfonic acid and 2-allyoxy-2-hydroxypropane-sulfonic acid. In some embodiments, the monomer comprises a hydrophobic moiety. In some embodiments, the monomer comprises a hydrophilic moiety.

Coatings for Medical Devices

A coating for a medical device, according to one embodiment of the present invention, comprises a block copolymer including two or more polymer blocks and one or more active agents. In some embodiments, the block copolymer comprises two blocks. In some embodiments, the block copolymer comprises three blocks. In yet other embodiments, the block copolymer comprises three or more blocks.

During formation of a coating or medical device according to the invention the block copolymer phase-separates into two or more phase domains. The term "phase domain" as used herein refers to distinct regions in the polymer that can be characterized in terms of the properties of the co-polymer block from which the particular phase domain is formed. The microstructure and properties of a phase-separated domain is dependent, amongst other things, on the moieties from which the blocks of the phase domains are formed. In one embodiment, the phase-separated block copolymer comprises two or more phase domains. In some embodiments, the phase-separated block copolymer comprises two phase domains. In some embodiments, the phase-separated block copolymer comprises three phase domains. For example, an AB or ABA block copolymer can phase-separate into two phase domains, where one domain is comprised of A blocks and the other phase domain is comprised of B blocks, while a ABC block copolymer can phase-separate into A, B and C phase domains.

Block copolymers can possess unique properties that can be used to modulate the active agent release-rate profile and the mechanical properties of a coating layer for a medical device. For example, a block copolymer can result in a material that offers properties similar to those of a blend of two polymers, but which maintains miscibility when the two phases are insoluble with each other. When such a blend exists, the block copolymer has a microstructure with individual phase domains that are rich in the individual block components. Each phase of the block copolymer will have physical properties dependent on the properties of the homopolymer component from which it is comprised. In contrast, a random copolymer will tend to possess properties that are between the properties of the homopolymers made from each monomer. A block copolymer, however, can possess properties that neither of the homopolymers has. If the properties of the homopolymers are quite different, for example if one block is hydrophilic and the other block is hydrophobic, the blocks will tend to self-assemble. That is the blocks can, for example, form micelles and aggregates in solution or micro-phase segregate in the solid state yielding phase domains with distinct properties. Random copolymers do not have this biphasic morphology or resultant properties.

The phase-separated block copolymer of the present invention can phase-separate on a nano-scale or a micro-scale. In some embodiments, at least one of the phase domains phase-separates on the nano-scale. In other embodiment, at least one of the phase domains phase separates on the micro-scale. The size of individual phase domains within a phase-separated block copolymer will depend on the size of the polymer blocks forming the phase domains. In some embodiments, the representative dimension (e.g., size of lamella or "particle") of a phase domain of the present invention is between 5 nm and 500 nm. In some embodiments, it can be between 50 and 400 nm; between 100 and 300 nm; or between 150 and 250 nm. Dimension is intended to mean measurement from the widest peak points.

Phase-separation of a block copolymer to yield an inhomogeneous material can be used to form a coating layer for a medical device, such as a drug delivery or eluting stent, with unique mechanical properties, and also to tailor active agent release-rates. The nano- or microstructure and properties of the phase-separated domains can be used to modulate the release-rate profile of a coating comprising one or more active agents. For example, by selecting the phase into which an active agent is preferentially incorporated the active agent release-rate can be modulated. The coating layers and methods of the present invention may be used to either decrease or increase the active agent release-rate from a coating layer. The methods of the invention may further be used to engineer coating layers that comprise two or more active agents where at least one of the active agents has a fast release-rate and at least one of the active agents has a slow release-rate, as desired.

In some embodiments, the phase-separated block copolymer of the coating layer for medical devices forms a polymer matrix in which one or more active agent is incorporated by being blended or mixed with, dissolved in, impregnated, trapped or distributed. The phase-separated block copolymers of the present invention can be used to accommodate otherwise incompatible drugs and/or to modulate the release-rates of one or more active agents from the coating layers by selecting the blocks forming the polymer matrix and the phase domains into which the block copolymer phase separates. In some embodiments, an active agent will preferentially be incorporated in one of the phase domains of the polymer matrix. For example, in a phase-separated block copolymer comprising hydrophobic and hydrophilic phase domains, an active agent that is hydrophobic will dissolve in the hydrophobic phase while a hydrophilic active agent will be preferentially incorporated in the hydrophilic domains. While the hydrophobic active agent will slowly leach out of the hydrophobic phase, the active agent in the hydrophilic phase will be released more quickly (e.g., in aqueous solution such as blood, etc.). In a coating comprising a single active agent, the release-rate of an active agent can be modulated by tailoring the phase domain into which the active agent is incorporated and/or incorporating phase domains in the polymer matrix that increase or decrease the release-rate of the active agent from the coating. For example, the release-rate of a hydrophobic active agent from a coating layer comprising a hydrophobic polymer matrix can be modulated by incorporating hydrophilic domains into the polymer matrix using a phase-separated block copolymer of the present invention, whereby the hydrophilic domains will increase the diffusion of water into the coating and active agent out of the coating.

The phase-separation of the block copolymer of the present invention can depend, among other factors, on the moieties from which the blocks are formed, on the nature of the blocks forming the copolymer, the interactions between those blocks and the environment and processing conditions used to form the coating layer. Suitable driving forces that can be used to induce phase-separation in the block copolymers of the present invention include, but are not limited to, the nature of the polymeric blocks, the size of blocks, ratio of moieties in the blocks, the block architecture (AB, ABC, ABA, etc), interactions between moieties within a block, hydrophilic or hydrophobic properties of a block, crystallinity of one of the phase domains, specific interactions in one of the phase domains, and the like. Phase-separation of a block copolymer of the present invention can also be controlled or enhanced by the choice of processing parameters used to form the coating layer. Suitable processing parameters useful to induce or control the phase-separation of block copolymer coatings of the present invention include, but are not limited to, choice of solvent or solvent mixture, differential evaporation rate of a solvent mixture, thermal cycles, and chemical incompatibility of the ingredients. A simple thermal cycle includes heating to a temperature at a given rate, holding that temperature for a given time and cooling down to a final temperature at a given rate. A more complex cycle would have several cooling, holding and heating intervals. This type of cycling (heat, cool, heat, cool, etc.) if chosen correctly can accelerate crystallization.

The block copolymers of the present invention can phase-separate into phase domains that include, but are not limited to, hydrophilic, hydrophobic, crystalline, semi-crystalline, non-crystalline, amorphous, hard, soft, hydrogen bonded, Π-Π stacked (e.g. of aromatic rings), and orientated. In one embodiment, the phase-separated block copolymer comprises hard phase domains. In one embodiment, the phase-separated block copolymer comprises soft phase domains. In one embodiment, the phase-separated block copolymer comprises a hydrophilic phase domain. In one embodiment, the phase-separated block copolymer comprises a hydrophobic phase domain. In other embodiments, the block copolymer phase-separates into hydrophilic and hydrophobic phase domains. In some embodiment, the phase-separated block copolymer comprises a crystalline phase domain. In some embodiments, one of the phase domains of the phase-separated block copolymer is hydrogen bonded. In yet other embodiments, the block copolymer phase-separates into two or more phase domains, where at least one of the phase domains is physically crosslinked by hydrogen bonds. In some embodiments, one of the phase domains of the phase-separated block copolymer is Π-Π stacked.

In some embodiments, the phase-separated block copolymer of the coating layer comprises hard and soft phase domains. The term "hard phase domain" as used herein refers to a phase domain comprising essentially polymer segments that are rigid and capable of forming strong intermolecular interactions. Hard phase domains can be formed, for example, by Π-Π interactions and stacking of moieties of the copolymer blocks or derived from a rigid block moiety such as an isocyanate. The term "soft phase domain" as used herein refers to a phase domain comprising essentially polymer segments having glass transition temperatures lower than the temperature of use. A soft phase domain can be derived, for example, from a block moiety such as a polyol. A soft phase domain can provides a coating with properties of an elastomer to prevent or at least reduce cracking of the coating, while hard phase domains can provide a coating with mechanical strength. Thus, a block copolymer coating that phase-separates into hard and soft phase domains will provide a tough elastomer with a high modulus for mechanical integrity, as well as large deformation at rupture that maintains the coating integrity during expansion. One example of a block copolymer coating useful in the practice of the present invention that phase separates into hard and soft phase domains is polystyrene-block-polyisobutylene-block-polystyrene copolymer. Π-Π stacking of the aromatic rings of the styrene blocks creates hard domains linked by soft isobutylene domains. A small molecule active agent, such as everolimus, will preferentially be accommodated in the soft isobutylene phase domains. Other examples of phase-separated block copolymers comprising hard and soft phase domains include, but are not limited to, the block copolymer of poly(L-lactide) and trimethylene carbonate (TMC), where the polylactide blocks crystallize to form hard phase domains and the TMC forms soft phase domains. Examples of polymer blocks that can be used to form hard phase domains include, but are not limited to, styrene, PLA, polyurethanes, methylmethacrylate, ethylmethacrylate, methacrylic acid, and hydroxyethyl methacrylate. Examples of polymer blocks that can be used form soft domains include, but are not limited to, isobutylene, TMC, PEG, polyols, vinyl pyrrolidinone and butyl methacrylate and other acrylate/methacrylates bearing long alkyl side chains.

In some embodiments, the phase-separated block copolymer of the coating layer comprises hydrophobic and hydrophilic phase domains. A block copolymer that comprises both hydrophobic and hydrophilic domains can be used to accommodate otherwise incompatible active agents in coating compositions for the medical devices of the present invention. A block copolymer comprising hydrophilic and hydrophobic blocks can be used to help the dissolution of a hydrophilic active agent, such as a peptide, into a coating composition comprising an organic solvent. For example, when a block copolymer comprising both hydrophilic and hydrophobic blocks is used in the coating compositions of the present invention, the spray coating of both a hydrophobic active agent, such as everolimus, and a hydrophilic active agent, such as a RGD or a VEGF peptide sequence, can be accomplished. While not being bound by any theory, apparently the hydrophilic polymer blocks will form micelles that allow the hydrophilic active agent to stay in solution and be spray coated. After coating, the block copolymer phase-separates into hydrophilic phase domains, including the peptide and hydrophobic phase domains comprising the hydrophobic active agent. In alternative embodiments of the present invention, a hydrophilic active agent can be swell-loaded into the hydrophilic phase domains of a coating layer comprising a phase-separated block copolymer coating of the present invention. For example, in a phase-separated block copolymer comprising hydrophobic and hydrophilic phase domains, an active agent such as everolimus will dissolve in the hydrophobic phase while a hydrophilic active agent, such as a peptide, can be swell loaded into the hydrophilic domains. Everolimus will slowly be released from the hydrophobic matrix domains, while the hydrophilic peptide will be released more quickly. Swell loading offers the ability to load a delicate active agent, such as a peptide, that is sensitive to temperature and/or solvents used to form the coating layers.

Examples of hydrophilic blocks for use in the copolymers of the present invention include, but are not limited to, hyaluronic acid (HA), heparin, polyethylene glycol (PEG), PEG acrylate and poly(vinyl pyrrolidinone) (PVP). Examples of hydrophobic blocks for use in the copolymers of the present invention include, but are not limited to, methacrylate copolymers such as, for example, methylmethacrylate, ethylmethacrylate, and butylmethacrylate, vinyl polymers such as, for example, polyethylene and PVDF, and polyesters such as, for example, polylactic acids (PLA). Examples of the synthesis of block copolymers comprising hydrophilic and hydrophobic blocks are described, for example, in U.S. Pat. Application Publication Nos. 2005/0147647 and 2005/0266038 to Glauser et al., the disclosures of which are incorporated herein by reference.

In a coating layer comprising a single hydrophobic active agent, a phase-separated block copolymer comprising hydrophilic phase domains can be used to modulate the release-rate of the hydrophobic active agent from the coating layer. The hydrophobic active agent will be incorporated in the non-hydrophilic phase domains of the coating layer. The hydrophilic phase domains of the coating layer will increase the diffusion of water into the coating and active agent out of the coating. Further, if a phase domain of a block copolymer is water miscible, in the presence of water that phase will have a tendency to preferentially be present at the surface. Hence, in an aqueous medium the hydrophilic blocks of a block copolymer will tend to migrate to the surface to yield a hydrophilic surface formed from those phase separated blocks. This driving force can be used to modulate the release rate of active agents from the coatings, as well as provide beneficial mechanical properties to the coating.

In one embodiment of the present invention, a PEG-PLA block copolymer will phase separate into PEG rich and PLA rich phase domains. The PLA can include at least one of poly(D,L-lactic acid), poly(D-lactic acid) or poly(L-lactic acid), or any combination thereof. The degree of phase-separation within the layer will be dependent, among other factors, on the relative block sizes. The PLA blocks will tend to increase the driving force for phase separation since the stereoregular PDLA or PLLA blocks will tend to form crystalline phase domains. This provides a strong driving force for phase separation that can lead to the formation of a surface that is rich in hydrophilic PEG blocks of the copolymer. Further, the PLA blocks of the copolymer also impart beneficial mechanical properties to the coating layer by providing mechanical integrity. Examples of the synthesis of block copolymers of PEG and PLA are describe in U.S. Pat. Application Publication No. 2005/0112170 to Hossainy et al., the disclosure of which is incorporated herein by reference.

In yet other embodiments of the invention, hydrogen bonding can be used to induce the phase-separation of the block copolymer matrix. Hydrogen bonding can be either intramolecular bonds between moieties of a block or inter-molecular between blocks. Also, physical crosslinking of a phase domain can be achieved by specific hydrogen bonding between copolymer blocks similar to those formed between DNA strands. Blocks of a copolymer that can form hydrogen bonds will phase separate into hydrogen bonded phase domains. These phase domains will repel active agents or other compounds that cannot form hydrogen bonds with the phase domain. Hence an active agent that can form hydrogen bonds, such as a peptide or oligonucleotide, will preferentially be incorporated in hydrogen bonded phase domains. Further, if an active agent can form hydrogen bonds with a phase domain, greater control over its release-rate will be realized because the release-rate will not be solely dependent on the diffusion of the active agent through the polymer matrix. Thus, in one embodiment, the release-rate of an active agent can be controlled by forming hydrogen bonded phase domains which incorporate the active agent. Further, the presence of hydrogen bonded phase domains can increase the mechanical integrity of a coating layer.

In some embodiments, phase-separation of the block copolymer can be controlled or enhanced by forming a coating layer from a coating composition comprising a solvent mixture where the solvent mixture comprises a fast evaporating solvent and a trailing solvent, and where a first block of the copolymer is marginally soluble in the fast evaporating solvent and soluble in the trailing solvent and a second block of the copolymer is poorly soluble in the trailing solvent and soluble in the fast evaporating solvent. The differential evaporation rate of the solvents from the coating composition will provide a driving force for phase-separation of the block copolymer during formation of the coating layer.

In some embodiments, the average molecular weights of the block copolymers of the present invention are between 60,000 and 2,000,000 Daltons (Da) or any range therein. More preferably, the molecular weight of the block copolymers is between 70,000 and 1,000,000 Da, between 70,000 and 500,000 Da, or between 100,000 and 300,000 Da. It is preferred that the block copolymers have an average molecular weight of at least 60,000 Da, and more preferably at least 100,000 Da to provide mechanical integrity to coating layers and the medical device of the present invention. At molecular weights above 60,000 Da, physical entanglement of the polymer chains can provide mechanical integrity to the coatings or the device body of the present invention.

The blocks of the copolymer of the present invention must be large enough so that the copolymer can phase separate into discrete phase domains. In one embodiment, a block of a block copolymer has a molecular weight of at least 1000 Da, alternately at least 3000 Da, or at least 4000 DA, or at least 5000 Da.

The size and weight ratio of blocks of the block copolymers of the present invention should be chosen to provide coating layers with mechanical integrity, adhesion to the underlying layer and controlled release of one or more active compounds. The weight percent ratio of the A and B blocks in an AB diblock copolymer are preferable from about 5% to 95% for the A block and 5% to 95% for the B block. In a BAB triblock copolymer the A blocks would preferably be between 5 and 30%, and combined B blocks would comprise about 70 to 95% by weight of the block copolymer. In a BAB block copolymer the B blocks may or may not be of the same size. In one embodiment, the B blocks would be approximately the same size. In some embodiments, the total molecular weight can be from 5,000 to 500,000 Da, preferably 40,000 to 150,000 Da.

The block copolymers of some embodiments comprise one or more hydrophilic polymeric blocks and one or more hydrophobic polymeric blocks. The hydrophilic blocks preferably comprises between 5 and 30% by weight and the hydrophobic blocks between about 70-95% by weight of the block copolymer. If the amount of the hydrophilic phase increases above about 30% weight the mechanical stability and integrity of the polymer matrix is greatly reduced, because in an aqueous environment, such as the blood stream, the hydrophilic polymer tends to absorb water and disintegrate. As a result, the release-rate of active agent from the hydrophilic phase will be greater than from the hydrophobic phase because of the ability of the hydrophilic phase to absorb water. This property of hydrophilic phase domains can be used in invention embodiments to modulate the release rate of active agents.

A wide variety of polymer blocks can be used to form the block copolymer of the present invention. The blocks chosen for the copolymer matrix must be biocompatible and minimize irritation when implanted. The choice of the matrix components depends on numerous factors including, but not limited to, the interactions between the polymer blocks and the agent(s) and/or coating solvent(s), the biocompatibility of the polymer blocks, and the physical, mechanical, chemical and biological properties of the polymers blocks and copolymers. Performance parameters include, for example, the ability to adhere to the surface of the medical device, the toughness of the coating desired, the capacity for the loading concentration of an agent, and the rate of biodegradation and elimination of the composition from a subject, as well as the ability of the copolymer blocks to phase separate.

Each of the polymer blocks chosen for the polymer matrix can be either biostable or biodegradable. "Biodegradable" refers to polymers that are capable of being completely degraded and/or eroded when exposed to bodily fluids such as blood and can be gradually resorbed, absorbed and/or eliminated from the subject. The process of breaking down and eventual absorption and elimination of the polymer can be caused by, for example, hydrolysis, metabolic processes, bulk or surface erosion, and the like. After biodegradation traces or residual polymer may remain on the device or near the device. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, a glycol, an anhydride, a lactic acid, a glycolic acid, a lactide, a glycolide, an ethylene oxide, an ethylene glycol, or combinations thereof. In some embodiments, the polymer matrix releases active agent during biodegradation. In other embodiments, the polymer matrix releases active agent without biodegradation of the matrix. In yet other embodiments, the release of active agent may be partially dependent on biodegradation of the polymer matrix. Biostable polymers should have a relatively low chronic tissue response.

The blocks of the block copolymer of the present invention can be formed from a wide variety of homopolymers or random copolymers. Representative examples of polymers that can be used in blocks of the block copolymer of the present invention include, but are not limited to, homopolymers and random copolymers based on acrylic polymers and copolymer (such as polyacrylonitrile, poly(acrylic acid), poly(methyl methacrylate), poly(hydroxyethyl methacrylate) and poly(butyl methacrylate)), poly(cyanoacrylates), fluorinated polymers or copolymers (such as polyfluoro-alkylenes, polyvinylidene fluoride, hexafluoropropene and polytetrafluoroethylene), homopolymers or random copolymers of hydroxyalkanoates (such as polycaprolactones, polylactides (such as poly(D-lactides), poly(L-lactides), poly(D,L-lactides)), poly(glycolic acid), poly(trimethylene carbonate), poly(hydroxyvalerate), poly(hydroxybutyrates), poly(dioxanones), poly(orthoesters) and polyvalerate), homopolymers or copolymers of poly(amino acids), polyanhydrides, polyphosphoesters, polyphosphoester urethanes, polyphosphazenes, polycarbonates, polyiminocarbonates, polyethylene oxide, poly(alkylene oxalates), polyurethanes, silicones, polyesters, polyolefins (such as polyethylene and polypropylene), poly(isobutylene) and ethylene-alphaolefin copolymers, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), ethylene vinyl alcohol copolymers (such as ethylene vinyl alcohol co-polymer, commonly known by the generic name EVOH or by the trade name EVAL®), polyamides (such as Nylon 66 and polycaprolactam), alkyd resins, polyoxymethylenes, polyimides, polyester amides, polyethers including poly(alkylene glycols) (such as poly(ethylene glycol) and poly(propylene glycol)), poly(tyrosine derived carbonates), poly(tyrosine derived arylates), epoxy resins, rayon, rayon-triacetate, biomolecules (such as fibrin, fibrinogen, starch, cellulose, collagen, hyaluronic acid), poly(N-acetylglucosamine) (chitin), chitosan, cellulose, cellulose acetate, cellulose butyrate, cellulose acetate butyrate, CELLOPHANE, cellulose nitrate, cellulose propionate, cellulose ethers, and carboxymethyl-cellulose, and derivatives and combinations of the foregoing. In some embodiments, the polymer can exclude any one or any combination of the aforementioned polymers.

In some embodiments, the phase-separated block copolymers comprise two or more hydrophobic polymer blocks. In some embodiments, the phase-separated block copolymers comprise a hydrophilic polymer block. In other embodiments, the phase-separated block copolymers comprise a hydrophilic block and one or more hydrophobic polymer blocks. In some embodiments, the phase-separated block copolymers comprise only hydrophobic polymer blocks.

Hydrophobic polymeric blocks for use in the block copolymer of the present invention include, but are not limited to, those derived from unsaturated monomers, for example, unsubstituted and substituted acrylates or vinyl monomers having the general formula $CH_2=CX-M$, where X is hydrogen or methyl and M is a substituted or unsubstituted aryl group or an ester group $O=C(OR)-$, where R is an alkyl or aryl group. Examples of hydrophobic blocks include, but are not limited to, methacrylate copolymers (such as methyl methacrylate, ethyl methacrylate, butyl methacrylate (BMA), lauryl methacrylate), vinyl polymers (such as polyethylene, polyvinylidene fluoride (PVDF), styrene(vinyl benzene)), or polyesters (such as polylactic acids (PLA)).

Other examples of hydrophobic polymers for the hydrophobic polymer blocks include, but are not limited to, homopolymers and random copolymers of poly(ester amide), polystyrene, polyisobutylene, polycaprolactone (PCL), poly (lactic acids) (PLA) and derivatives of PLA, poly(L-lactic acid), poly(D,L-lactic acid), poly(D-lactic acid), poly(glycolide), polyalkylene, polyfluoroalkylene, polyhydroxylkanoate, poly(3-hydroxybutyrate), poly(4-hydroxybutyrate), poly(3-hydroxyvalerate), poly(3-hydroxyhexanoate), poly (4-hydroxyhexanoate), mid-chain polyhydroxyalkanoate, poly(trimethylene carbonate), poly(ortho ester), polyphosphazenes, poly(phosphoester), poly(tyrosine derived arylates), poly(tyrosine derived carbonates), polydimethyloxanone (PDMS), polyvinylidene fluoride (PVDF), polyhexafluoropropylene (HFP), polydimethylsiloxane, polychlorotrifluoroethylene), acrylic polymers which cover the acrylates and methacrylates, poly(butyl methacrylate), poly(methyl methacrylate), poly(methacrylates), poly(2-hydroxyethyl methacrylate), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly(urea-urethanes), and derivatives and combinations of the foregoing. In some embodiments, the polymer can exclude any one of the aforementioned polymers.

Hydrophilic polymeric blocks for use in the block copolymer of the present invention include, but are not limited to, those derived from unsaturated monomers, for example, unsubstituted and substituted acrylates or vinyl monomers having the general formula $CH_2=CX-M$, where X is hydrogen or methyl and M is a substituted or unsubstituted aromatic group or an ester group $O=C(OR)-$, where R is hydrogen or a hydroxyalkyl group. Examples of hydrophilic blocks include, but are not limited to, hyaluronic acid, heparin, PEG acrylate and poly(vinyl pyrrolidinone).

Other examples of hydrophilic polymers for the hydrophilic polymer blocks for the include, but are not limited to, homopolymers and random copolymers of hydroxylethyl methacrylate (HEMA), PEG acrylate (PEGA), PEG methacrylate, 2-methacryloyloxyethylphosphorylcholine (MPC) and n-vinyl pyrrolidone (VP), poly(vinyl pyrrolidone) (PVP), carboxylic acid bearing monomers such as methacrylic acid (MA), acrylic acid (AA), hydroxyl bearing monomers such as hydroxypropyl methacrylate (HPMA), hydroxypropylmethacrylamide, alkoxymethacrylate, alkoxyacrylate, and 3-trimethylsilylpropyl methacrylate (TMSPMA), poly(ethylene glycol) (PEG), poly(propylene glycol), PLURONIC™ surfactants (polypropylene oxide-co-polyethylene glycol), poly(tetramethylene glycol), hydroxy functional poly(vinyl pyrrolidone), polyalkylene oxide, dextran, dextrin, sodium hyaluronate, hyaluronic acid, heparin, elastin, chitosan, and derivatives and combinations thereof. In some embodiments, the polymer can exclude any one of the aforementioned polymers.

The polymer coatings and devices comprising the phase-separated block copolymers of the present invention can be characterized by any method know in the art such as, for example, differential scanning calorimetry (DSC), scanning electron microscopy, atom force microscopy, Raman microscopy, and X-ray or neutron scattering. Differential scanning calorimetry is a particularly useful method to characterize the phase separation of the block copolymers of the devices and coatings. Where the copolymer blocks are phase-separated the individual thermo-physical properties, such as glass transition temperature (Tg), will be separately observed. If the blocks have not phase separated a single intermediate Tg will be observed. Scanning electron microscopy and atom force microscopy may be used for visual characterization of the phase separation depending on the size of the different phase domains.

Methods of Forming Coating Layers and Devices

A coating layer for a medical device, such as a stent, according to one embodiment of the present invention comprises a phase-separated block copolymer and one or more active agents. This layer can also be referred to as a reservoir layer. Optionally, the coating layer may further comprise one or more additives or other components such as, for example, plasticizing agents, metals, metal oxides or ceramics.

Typically, coating layers for a medical device are formed by blending one or more active agents together with the block copolymer dissolved in a solvent to form a coating composition, applying the coating composition to a medical device surface (also referred herein to as a substrate) by a method such as casting, spraying, dipping or immersing, direct dispensing by hand or injection. After applying the composition to the device surface the wet coating is dried by removing the solvent to leave on the device surface active agent(s) dispersed in one or more of the domains of the phase-separated block copolymer matrix. Phase-separation can be induced in the block copolymer after applying the coating composition to the substrate, by either the physical properties of the polymer blocks or by process conditions. The wet coating can be dried by allowing the solvent to evaporate at ambient or elevated temperature. Solvent removal may also be accomplished by using a method such as vacuum, freeze drying or critical point drying. Alternatively the active agent can be swell-loaded into a phase domain, such as a hydrophilic domain, after formation of the coating layer. Swell loading is a preferred method where an active agent, such as a peptide, is sensitive to process conditions.

Coating compositions are prepared by conventional methods, wherein all components are combined and then blended. More particularly, adding a predetermined amount of a block copolymer to a predetermined amount of a compatible solvent or mixture of solvents forms a polymer solution. The block copolymer can be added to the solvent at ambient pressure, and under anhydrous or other atmosphere. If necessary, gentle heating and stirring or mixing can cause the polymer to dissolve into the solvent, for example, 12 hours in a 60° C. water bath. Sufficient amounts of active agent are dispersed in the blended block copolymer solution. The active agent preferably should be in true solution or saturated in the blended composition. If the active agent is not completely soluble in the composition, operations including mixing, stirring, or agitation can be employed to homogenize the residuals. The dissolution of a hydrophilic active agent in organic solvents can be improved by using a block copolymer comprising hydrophilic blocks that can form micelles which allow the active agent to stay in solution, as described herein. Alternatively, active agent can first be added to a compatible solvent before mixing with the polymer solution. Optionally, a second solvent, such as tetrahydrofuran or dimethylformamide, can be used to improve the solubility of an active agent in the coating composition or to increase the composition's wetting ability. The second solvent can be added to the coating composition or the active agent can be added to the second solvent before mixing with the polymer solution. If additives and other components, for example, plasticizers, metals, metal oxides or ceramics are used, these may be added and blended with the coating composition at any step.

The block copolymer can comprise from about 0.1% to about 35%, and more narrowly from about 2% to about 20% by weight of the total weight of the coating composition. The one or more solvents may comprise from about 19.8% to about 99.8%, more narrowly from about 49% to about 87%, and yet more narrowly from about 79% to about 87% by weight of the total weight of the coating compositions. The one or more active agents may comprise from about 0.02% to about 40%, preferably from about 0.1% to about 9%, and more narrowly from about 0.7% to about 1.2% by weight of the total weight of the coating composition. Selection of a specific weight ratio of the polymer to solvent depends on factors such as, but not limited to, the material from which the device is made, the geometrical structure of the device, and the type and amount of active agent employed. The specific weight percent of an active agent depends on the block copolymer—active agent morphology of the coating layer and factors such as the dosage, duration of the release, cumulative amount of release, and the release-rate desired.

The coating composition after being deposited on a device surface is referred to as a "wet coating layer." After coating the medical device solvent remaining in the wet coating layer is removed to form a dry coating layer. As used herein the term "wet coating layer" refers to a coating composition comprising solvent that has been applied to the surface of a device. A coating layer is referred to as wet until essentially all the solvent is removed from the coating layer. It is understood that by drying substantially all the solvent and wetting fluid (if used) will be removed from the coating layer, but traces or residues can remain blended with the polymer. Suitable methods for removing solvents and wetting fluids from the coating composition include, but are not limited to, evaporation, freeze-drying (sublimation), non-solvent exchange, critical point drying, or any combination thereof. Evaporation of the solvent can occur at room temperature or be induced by heating the device to a temperature for a period of time. The heating temperature is chosen so as not to exceed temperatures at which the active agent is adversely affected. Removal of the solvent may occur in a controlled atmosphere, for example humid, anhydrous or solvent saturated, at ambient pressure or under vacuum. The temperature at which the solvent is removed will depend on the method, and may vary over a wide range. Conditions should be chosen so that they do not substantially adversely affect active agents or other coating layer properties.

As described above, differential evaporation rates of a solvent mixture can be used to control and/or induce the phase-separation of the block copolymers of the present invention. For example, the phase-separation can be controlled or enhanced by using a solvent mixture comprising a fast evaporating solvent and a trailing solvent, where the first component is marginally soluble in the fast evaporating solvent and soluble in the trailing solvent, while the second component is poorly soluble in the trailing solvent. The differential evaporation rates of the solvents will provide a thermodynamic driving force for phase separation. A solvent saturated atmosphere may also be used to control the evaporation of a solvent to induce phase-separation.

In some embodiments, a hydrophilic active agent can be swell-loaded into the hydrophilic domains of a phase-separated block copolymer coating layer. This can be accomplished, for example, by soaking the coating layer in a solution of a peptide and then drying the layer. This is beneficial when the active agent, such as a peptide, is sensitive to processing conditions or solvents. When swell coating in water, water enters the hydrophilic phase along with the hydrophilic active agent. The coating is subsequently dried. This method is useful for forming devices with more delicate active agents that are sensitive to temperature, solvents, and other process conditions.

After drying the coating layer one or more post-formation treatments may be performed to the coating layers and medical devices of the present invention. Optional post-processing steps include, but are not limited to, annealing the coating layer, applying a protective coating, applying a rate-reducing membrane, diffusion barrier layer or top-coat layer to the coating layer surface, applying an optional finishing coat layer, and sterilization. The medical devices may further comprise an optional top-coat or barrier layer that, in some embodiments, controls or modulates the diffusion of the active agent out of the coating layer. Outer coating layers can be applied over all or only a portion of the coating layer comprising the active agent. Examples of topcoat layers and finishing coat layers are described, for example, in U.S. Patent Application Publication No. US 2005/0191332 to Hossainy, the disclosure of which is incorporated herein by reference. Further examples of outer layers, including rate-reducing membranes and diffusion barrier layers, are described in U.S. Pat. No. 6,908,624 to Hossainy et al., the disclosure of which is incorporated herein by reference. Some embodiments anneal the coating layer to remove stresses. In these or other embodiments, annealing ameliorates coating layer brittleness caused by, for example, freeze-drying.

A primer layer may optionally be used in the embodiments of the present invention to aid the adhesion of the coating layer to the device surface. A primer layer can improve the adhesion of the polymer-active agent coating to the medical device. This is particularly useful when the presence or concentration of the active agent in the polymer matrix interferes with the ability of the polymer matrix to adhere effectively to the device surface. If an optional primer layer is used, the primer layer is coated on the device or a portion of the device by any method described herein or known to one of ordinary skill in the art. The primer layer can be dried (solvent removed) and/or cured before the coating composition comprising the polymer matrix and active agent is applied to the surface of the primer layer. Primer compositions may be prepared by adding a predetermined amount of one or more polymers to a predetermined amount of solvent or mixture of solvents. Representative examples of polymers for the primer layer include, but are not limited to, polyisocyanates, polyethers, polyurethanes, acrylates, titanates, zirconates, silane coupling agents, high amine content polymers, polymers with a high content of hydrogen bonding groups, and unsaturated polymers and prepolymers. Representative examples of polymers also include those polymers used in the polymer matrices of the present invention as described herein. Further examples of primer layers useful for the medical devices of the present invention include those disclosed in U.S. Pat. No. 6,908,624 to Hossainy et al., the disclosure of which is incorporated herein by reference.

Coating layer thickness can be from about 1.0 nm to about 1.0 mm, from about 1.0 nm to about 100 µm, from about 1.0 nm to about 1.0 µm, from about 1.0 nm to about 100 nm, from about 1.0 nm to about 10 nm, from about 10 nm to about 100 nm, from about 0.5 µm to about 10 µm, from about 1 µm to about 10 µm, from about 10 µm to about 50 µm, from about 50

μm to about 100 μm, or any range therein. In other embodiments, the thickness of the coating layer can be regionally distributed throughout a device to create a variation in thicknesses such as, for example, the variation in thicknesses present in an abluminally-coated, drug-eluting stent systems.

Solvent

The solvent for the coating compositions should be capable of dissolving the block copolymer and active agents at the concentration desired in the coating solution. Any suitable solvent, blend or mixture of one or more solvents that meets the criteria for a coating solvent can be used. Solvents useful for forming the coating compositions of the present invention are chosen based on factors such as, for example, the solubility of the block copolymer in the solvent, compatibility with the active agents, the volatility of the solvent, the effect of the solvent on inducing phase separation, as described herein, and the ability of the solvent to be removed from the coating layer without altering the phase-separation or distribution of active agents.

Examples of suitable solvents for the practice of the present invention include, but are not limited to, dimethylacetamide, dimethylformamide, tetrahydrofuran, cyclohexanone, acetone, acetonitrile, i-propanol, n-propanol, methanol, ethanol, butanol, propylene glycol monomethyl ether, methyl butyl ketone, methyl ethyl ketone, diethyl ketone, ethyl acetate, n-butyl acetate, dioxane, chloroform, water (buffered saline), dimethylsulfoxide, dimethylformide, benzene, toluene, xylene, hexane, cyclohexane, pentane, heptane, octane, nonane, decane, decalin, i-butyl acetate, i-propyl acetate, diacetone alcohol, benzyl alcohol, 1-butanone, 2-butanone, N-methylpyrrolidinone, methylene chloride, carbon tetrachloride, tetrachloroethylene, tetachloroethane, chlorobenzene, 1,1,1-trichloroethane, formamide, hexafluoroisopropanol, 1,1,1-trifluoroethanol, hexamethyl phosphoramide, and combinations thereof.

Active Agents

The coating compositions of the present invention comprise one or more active agents. The term "active agent" refers to any agent that is capable of providing a therapeutic, prophylactic or other biological effect within a patient. An active agent can also be a diagnostic agent, or be for enhancing wound healing in a vascular site or improving the structure and elastic properties of a vascular site. A wide range of different active agents can be incorporated into the medical devices of the present invention. Examples of suitable active agents include, but are not limited to, synthetic inorganic and organic compounds, proteins, peptides, polysaccharides and other sugars, lipids, and oligonucleotides, and DNA and RNA nucleic acid sequences, and the like. If combinations of active agents are used, each agent is chosen with regard to its compatibility with other agents and/or phase domains and blocks of the copolymers, and with regard to its medical effect and release-rate from the copolymer. An active agent can be a drug.

Active agents with a wide range of molecular weights, for example, between 100 and 500,000 grams per mole are useful in the embodiments of the present invention. The amounts of the one or more active agents in the embodiments of the present invention should be at the dosage or concentration required to produce a therapeutic effect, and greater than the level at which non-therapeutic effects are obtained. The dosage or concentration of the active agent depends upon factors such as, for example, the particular circumstances of the subject, the nature of the trauma, the nature of the therapy desired, the time over which the ingredient administered resides at the vascular site, and if other bio-active substances are employed, the nature and type of the substance or the combination of substances. The therapeutically effective dosage can be determined by methods known in the art, such as for example, conducting suitable in vitro studies. For example, the active agent can be incorporated into the polymeric matrix in a percent loading of between 0.01% and 70%, alternatively, between 5% and 50% by weight.

The active agents can be blended or mixed with the block copolymer in the coating composition and/or an active agent can be swell-loaded into the phase-separated polymer coating or device as described herein. Active agents of the coating compositions may or may not form linkages with the polymer matrix in the medical devices and coatings of the present invention. If linkages form, the connections may be physical, chemical, or a combination thereof. Examples of physical connections include, but are not limited to, an interlinking of components that can occur, for example, in interpenetrating networks and chain entanglement. Examples of chemical connections include, but are not limited to, covalent and non-covalent bonds. Non-covalent bonds include, but are not limited to, ionic bonds and inter-molecular attractions such as, for example, hydrogen bonds and electrostatic interactions or attractions. In one embodiment, the formation of hydrogen bonds between the active agent and one of the polymer phase domains is used to modulate (tailor) the release-rate of the active agent from the coating layer. If more than one agent is present in the coating, each agent may form a different type of linkage or no linkage.

Active agents useful in the practice of the embodiments of the present invention include, but are not limited to, antiproliferative, antineoplastic, anti-inflammatory, steroidal anti-inflammatory, non-steroidal anti-inflammatory, antiplatelet, anticoagulant, antifibrin, antithrombin, antimitotic, antibiotic, antiallergic, antioxidant, and cytostatic agents, and combinations thereof.

Examples of antiproliferative substances include, but are not limited, to actinomycin D, or derivatives and analogs thereof (manufactured by Sigma-Aldrich of Milwaukee, Wis., or COSMEGEN available from Merck, Whitehouse Station, N.J.). Synonyms of actinomycin D include dactinomycin, actinomycin IV, actinomycin $I_1$, actinomycin $X_1$, and actinomycin $C_1$. Examples of antineoplastics and/or antimitotics include, but are not limited to, paclitaxel (e.g. TAXOL® by Bristol-Myers Squibb Co., Stamford, Conn.), docetaxel (e.g. TAXOTERE®, from Aventis S.A., Frankfurt, Germany), methotrexate, azathioprine, vincristine, vinblastine, fluorouracil, doxorubicin hydrochloride (e.g. ADRIAMYCIN® from Pharmacia & Upjohn, Peapack, N.J.), and mitomycin (e.g. MUTAMYCIN® from Bristol-Myers Squibb Co., Stamford, Conn.). Examples of antiplatelets, anticoagulants, antifibrins, and antithrombins include, but are not limited to, heparin, sodium heparin, low molecular weight heparins, heparin sulfate, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX™ (Biogen, Inc., Cambridge, Mass.), and 7E-3B® (an antiplatelet drug from Centocor, Horsham, Pa.). Examples of suitable antimitotic agents include, but are not limited to, methotrexate, azathioprine, vincristine, vinblastine, fluorouracil, adriamycin, and mutamycin. Examples of such cytostatic or antiproliferative agents include, but are not limited to, angiopeptin, angiotensin converting enzyme inhibitors such as captopril (e.g. CAPOTEN® and CAPOZIDE® from Bristol-Myers Squibb Co., Stamford, Conn.), cilazapril or lisinopril (e.g. PRINIVIL® and PRINZIDE® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name MEVACOR® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include, but are not limited to, alpha-interferon, genetically engineered epithelial cells, tacrolimus, dexamethasone, and rapamycin and structural derivatives or functional analogs thereof, such as 40-O-(2-hydroxy)ethyl-rapamycin (known by the trade name of everolimus available from Novartis Pharma AG, Switzerland), 40-O-(3-hydroxy)propyl-rapamycin, 40-O-[2-(2-hydroxy)ethoxy]ethyl-rapamycin, and 40-O-tetrazole-rapamycin.

In some embodiments, one or more of the active agents are water soluble. Water-soluble, small molecule active agents include, but are not limited to, proteins, peptides, biologically active compounds conjugated to peptides, anti-inflammatory, anti-proliferative, or antimicrobial drugs. Examples of peptides include, but are not limited to, RGD and a VEGF sequence. In one embodiment, the active agents include cyclic-RGD (c-RGD) peptide, poly(L-arginine), poly(D-arginine), poly(D,L-arginine), poly(L-lysine), poly(D-lysine), poly(δ-guanidino-α-aminobutyric acid), a mixture of poly(L-arginine) and poly(D-arginine), and elastin mimetic polypeptides. The term "cyclic RGD" refers to a peptide that is a product of condensation of arginine (amino acid R), glycine (aminoacetic acid or amino acid G), and aspartic acid (amino acid D), the peptide having a cyclic structure.

The terms "poly(L-arginine)," "poly(D-arginine)," "poly(D,L-arginine)" are intended to include L-, D-, and/or D,L-arginine in both its polymeric and oligomeric form. Polymers and/or oligomers of L-, D-, and/or D, L-arginine that can be used comprise a plurality of repeating monomeric amino acid units connected with peptide bonds, each unit including 1-guanidinopropyl radical having the structure —CH$_2$—CH$_2$—CH$_2$—NH—C(NH$_2$)=NH. In one embodiment, a heptamer (R7) (p=7) or a nonamer (R9) (p=9) of L-arginine can be used.

Elastin mimetic polypeptides are protein pentamers comprising a number of amino acids and having the formula:

-[(V/I)-P-G-Xaa-G]$_5$-, (I)

where V is valine (2-amino-3-methylbutyric acid), I is isoleucine (2-amino-3-methylvaleric acid), P is proline [(S)-2-pyrrolidine carboxylic acid], G is glycine (aminoacetic acid), and Xaa is an amino acid which is valine in the first four repeating units and either isoleucine or lysine [(S)-2,6-diaminohexanoic acid or K] in the fifth repeating unit. The abbreviation "V/I" signifies that either valine or isoleucine, but not both, can be present.

Example of diagnostic agents include, but are not limited to, those detectable by x-ray, fluorescence, magnetic resonance imaging, radioactivity, ultrasound, computer tomography (CT), and positron emission tomography (PET).

The foregoing substances are listed by way of example and are not meant to be limiting. Other active agents that are currently available or that may be developed in the future are equally applicable.

Medical Devices

As used herein, a "medical device" may be any device that can be used in the medical treatment of a human or veterinary patient. Medical devices may be used either externally on a patient or implanted in a patient. In preferred embodiments, the medical device is implantable, such as a drug eluting stent. Medical devices may be fully absorbable, such as an implantable fully absorbable sent. Examples of medical devices include, but are not limited to, stents, stent-grafts, vascular grafts, artificial heart valves, foramen ovale closure devices, cerebrospinal fluid shunts, pacemaker electrodes, guidewires, ventricular assist devices, cardiopulmonary bypass circuits, blood oxygenators, coronary shunts (AXIUS™, Guidant Corp., IN), vena cava filters, and endocardial leads (FINELINE® and ENDOTAK®, Guidant Corp., IN). The underlying structure of the medical device can be virtually any design. Preferably, the implantable medical device is a stent. Examples of stents include, but are not limited to, tubular stents, self-expanding stents, coil stents, ring stents, multi-design stents, and the like. In some embodiments, the stents include, but are not limited to, vascular stents, renal stents, biliary stents, pulmonary stents and gastrointestinal stents. While examples of coating a device such as a drug eluting stent are described herein, one of skill in the art will appreciate that other medical devices and substrates can be manufactured using the phase-separated block copolymers and methods of the present invention.

The medical device can be made of a metallic material or alloy, low-ferromagnetic, non-ferromagnetic, biostable polymeric, biodegradable polymeric, bioabsorbable polymers, biodegradable metallic or other compatible material known in the art. In some embodiments, the medical devices may be formed from a composition comprising a phase-separated block copolymer and one or more active agents by, for example, injection molding and other methods, as known to one skilled in the art. Examples of metals and alloys include, but are not limited to, ELASTINITE® (Guidant Corp., IN), NITINOL® (Nitinol Devices and Components, Fremont, Calif.), stainless steel, tantalum, tantalum-based alloys, nickel-titanium alloys, platinum, platinum-based alloys such as, for example, platinum-iridium alloys, iridium, gold, magnesium, titanium, titanium-based alloys, zirconium-based alloys, alloys comprising cobalt and chromium (ELGILOY®, Elgiloy Specialty Metals, Inc., Elgin, Ill.; MP35N and MP20N, SPS Technologies, Jenkintown, Pa.) or combinations thereof. The tradenames "MP35N" and "MP20N" describe alloys of cobalt, nickel, chromium and molybdenum. The MP35N consists of 35% cobalt, 35% nickel, 20% chromium, and 10% molybdenum. The MP20N consists of 50% cobalt, 20% nickel, 20% chromium, and 10% molybdenum.

While particular embodiments of the present invention have been described, it will be apparent to those skilled in the art that changes and modifications can be made without departing from the spirit and scope of the teachings and embodiments of this invention. One skilled in the art will appreciate that such teachings are provided in the way of example only, and are not intended to limit the scope of the invention. The specification and examples are thus exemplary only, with the true scope and spirit of the invention being set forth in the following claims and legal equivalents.

The invention claimed is:

1. A medical device comprising a phase-separated block copolymer of two or more polymer blocks and the medical device comprising two or more active agents;
   wherein the phase-separated block copolymer comprises two or more phase domains;
   wherein a first active agent is preferentially incorporated in a first phase domain and a second active agent is preferentially incorporated in a second phase domain, and wherein the first and the second active agents have different release-rate profiles from the two or more phase domains in the phase-separated block copolymer;

wherein the two or more phase domains of the phase-separated block copolymer comprise a hydrophobic phase domain which comprises a hydrophobic block and a hydrophilic phase domain which comprises a hydrophilic block;

wherein the first phase domain comprises the hydrophobic phase domain and the second phase domain comprises the hydrophilic phase domain;

or the first phase domain comprises the hydrophilic phase domain and the second phase domain comprises the hydrophobic phase domain;

wherein the hydrophilic block of the block copolymer comprises a hydrophilic constituent monomer selected from the group consisting of PEG acrylate (PEGA), PEG methacrylate, 2-methacryloyloxyethyl-phosphorylcholine (MPC), n-vinyl pyrrolidone (VP), alkoxymethacrylates, alkoxyacrylates, 2-methacryloylethyl phosphoryl choline, phosphoryl choline methacrylate, 2-acrylamido-2-methyl-1-propanesulfonic acid, 3-sulfopropyl acrylate, 3-sulfopropyl methacrylate (SPMA), vinylsulfonic acid, 4-styrenesulfonic acid, 2-allyoxy-2-hydroxypropanesulfonic acid, and combinations thereof;

and wherein the hydrophobic block of the block copolymer comprises a hydrophobic constituent monomer selected from the group consisting of 3-hydroxyhexanoate, 4-hydroxyhexanoate, and combinations thereof.

2. The medical device of claim 1, wherein the medical device is a stent.

3. The medical device of claim 1, wherein the medical device is fully absorbable.

4. The medical device of claim 1, wherein the medical device comprises a substrate and a coating, the coating comprising the phase-separated block copolymer and at least the first and the second active agents, wherein the coating is disposed on at least a portion of the substrate.

5. The medical device of claim 4, wherein the medical device further comprises a primer layer and the coating is disposed on at least a portion of the primer layer.

6. The medical device of claim 1, wherein the hydrophilic phase domain comprises hydrophilic polymer block(s), the hydrophilic polymer block(s) being block(s) of the block copolymer, and the block copolymer comprising between 5% and 30% by weight hydrophilic block(s).

7. The medical device of claim 1, wherein at least one active agent of the two or more active agents is a hydrophobic active agent and the release rate of the hydrophobic active agent from the medical device is increased by the hydrophilic phase domain.

8. The medical device of claim 1, wherein the release-rate of at least one of the two or more active agents of the medical device from the hydrophilic phase domain is greater than the release-rate of at least another of the two or more active agents of the medical device from the hydrophobic phase domain.

9. The medical device of claim 1, wherein the phase-separated block copolymer comprises a hard phase domain; and wherein the first phase domain comprises the hard phase domain, or wherein the second phase domain comprises the hard phase domain, or wherein the block copolymer comprises more than two phase domains and neither the first nor the second phase domain comprises the hard phase domain.

10. The medical device of claim 9, wherein the hard phase domain is crystalline.

11. The medical device of claim 9, wherein the hard phase domain comprises stacking of polymer moieties.

12. The medical device of claim 11, wherein the moieties of the hard phase domain are aromatic rings.

13. The medical device of claim 1, wherein the phase-separated block copolymer comprises a soft phase domain; and wherein the first phase domain comprises the soft phase domain, or wherein the second phase domain comprises the soft phase domain, or wherein the block copolymer comprises more than two phase domains and neither the first nor the second phase domain comprises the soft phase domain.

14. The medical device of claim 13, wherein at least one of the two or more active agents of the medical device is preferentially incorporated in the soft phase domain, and if the block copolymer comprises more than two phase domains and neither the first nor the second phase domain comprises the soft phase domain, then the medical device comprises three or more active agents.

15. The medical device of claim 1, wherein one of the phase domains is hydrogen bonded; and wherein the hydrophilic phase domain is hydrogen bonded, or wherein the block copolymer comprises more than two phase domains, and neither the first nor the second phase domain is hydrogen bonded.

16. The medical device of claim 15, wherein the hydrogen bonded phase domain comprises at least one of the two or more active agents of the medical device, wherein the active agent forms hydrogen bonds with moieties of the phase domain; and wherein if the block copolymer comprises more than two phase domains and neither the first nor the second phase domain comprises the hydrogen bonded phase domain, then the medical device comprises three or more active agents.

17. The medical device of claim 1, wherein one of the phase domains is crystalline.

18. The medical device of claim 1, wherein all or substantially all of the first active agent in the first phase domain is released in less than 15 days, and wherein all or substantially all of the second active agent in the second phase domain is released in a period of time greater than 15 days.

19. The medical device of claim 1, wherein the hydrophilic constituent monomer of the hydrophilic block of the block copolymer is selected from the group consisting of PEG acrylate (PEGA), PEG methacrylate, 2-methacryloyloxyethyl-phosphorylcholine (MPC), n-vinyl pyrrolidone (VP), and combinations thereof.

20. The medical device of claim 1, wherein the hydrophilic constituent monomer of the hydrophilic block of the block copolymer is selected from the group consisting of 2-acrylamido-2-methyl-1-propanesulfonic acid, 3-sulfopropyl acrylate, 3-sulfopropyl methacrylate (SPMA), vinylsulfonic acid, 4-styrenesulfonic acid, 2-allyoxy-2-hydroxypropanesulfonic acid, and combinations thereof.

21. The medical device of claim 1, wherein the hydrophilic block of the block copolymer comprises a second hydrophilic monomer selected from the group consisting of dextrin, elastin, 2-methacryloylethyl phosphoryl choline, phosphoryl choline, methacrylate, and combinations thereof.

* * * * *